(12) United States Patent
Han

(10) Patent No.: US 7,811,759 B2
(45) Date of Patent: Oct. 12, 2010

(54) METHOD FOR DETECTING NCRNA

(76) Inventor: Jian Han, 7712 Donegal Dr., Huntsville, AL (US) 35802

( * ) Notice: Subject to any disclaimer, the term of this patent is extended or adjusted under 35 U.S.C. 154(b) by 103 days.

(21) Appl. No.: 11/568,065

(22) PCT Filed: Apr. 20, 2005

(86) PCT No.: PCT/US2005/013247

§ 371 (c)(1),
(2), (4) Date: Sep. 24, 2007

(87) PCT Pub. No.: WO2005/103298

PCT Pub. Date: Nov. 3, 2005

(65) Prior Publication Data

US 2008/0166707 A1 Jul. 10, 2008

Related U.S. Application Data

(60) Provisional application No. 60/563,877, filed on Apr. 20, 2004.

(51) Int. Cl.
C12Q 1/68 (2006.01)
C07H 21/02 (2006.01)
C07H 21/04 (2006.01)
(52) U.S. Cl. .................. 435/6; 536/23.1; 536/24.3
(58) Field of Classification Search .......... 435/6; 536/22.1, 24.3
See application file for complete search history.

(56) References Cited

U.S. PATENT DOCUMENTS

| | | | | |
|---|---|---|---|---|
| 4,988,617 A * | 1/1991 | Landegren et al. | | 435/6 |
| 5,474,895 A | 12/1995 | Ishii et al. | | |
| 6,037,130 A * | 3/2000 | Tyagi et al. | | 435/6 |
| 7,189,507 B2 * | 3/2007 | Mack et al. | | 435/6 |
| 7,459,145 B2 * | 12/2008 | Bao et al. | | 424/9.32 |
| 2003/0129611 A1 * | 7/2003 | Bao et al. | | 435/6 |
| 2003/0198982 A1 * | 10/2003 | Seela et al. | | 435/6 |
| 2006/0105360 A1 * | 5/2006 | Croce et al. | | 435/6 |
| 2007/0020678 A1 * | 1/2007 | Ault-Riche et al. | | 435/6 |

FOREIGN PATENT DOCUMENTS

WO WO 90/01564 2/1990
WO WO01/13119 * 2/2001

OTHER PUBLICATIONS http://www.basic.northwestern.edu/biotools/oligocalc.html pp. 1-7.*
Marras et al. Multiplex detection of single-nucleotide variations using molecular beacons. Genetic Analysis : Biomolecular Engineering 14 : 151-156 (1999).*
Lagos-Quintana et al. Identification of novel genes coding for small expressed RNAs. Science 294 : 853-858 (2001).*
Bartel D.P., MicroRNAs : Genomics, Biogenesis, Mechanism, and Function : A Review Cell 116 : 281297 (2004).*
Mergny et al., Fluorescence energy transfer as a probe for nucleic acid structures and sequences. Nucleic Acids Research 22 (6) :920-928 (1994).*
Sokol et al., Realtime detection of DNA-RNA hybridization in living cells. PNAS 95 : 11538-11543 (1998).*
Calin, G.A. et al. Frequent deletions and down-regulation of micro-RNA genes miR15 and miR16 at 13q14 in chronic lymphocytic leukemia. Proceedings of the National Academy of Sciences of USA, National Academy of Science, Washington, DC, vol. 99, No. 23, Nov. 26, 2002, pp. 15524-15529.
Galvan, B. et al. Bioluminescence hybridization assays using recombinant aequorin. Application to the detection of prostate-specific antigen mRNA. Analytical Chemistry, American Chemical Society, vol. 68, No. 20, Oct. 15, 2006, pp. 3545-3550.
Schmittgen T D, A high-throughput method to monitor the expression of microRNA precursors, Nucleic Acids Research, 2004 vol. 32, No. 4.
Hakala, Harri, Simultaneous detection of several oligonucleotides by time-resolved flurometry: the use of a mixture of categorized microparticles in a sandwich type mixed-phase hybridization assay, Nucleic Acids Research, 1998,vol. 26, No. 24, 5581-5588.

* cited by examiner

*Primary Examiner*—Ethan Whisenant
(74) *Attorney, Agent, or Firm*—Bradley Arant Boult Cumming, LLP; T. Gregory Peterson; Nicholas J. Landau

(57) ABSTRACT

Described is a novel method for the detection of ncRNA molecules. The disclosed method is especially useful for the detection miRNA and siRNA. The method can be used to generate a profile of the ncRNA molecules present in a sample. In addition, using the methods of the present disclosure a ncRNA signature for a given disease or condition can be created. The ncRNA signature can be used for diagnostic purposes, therapeutic purposes and drug discovery purposes, as well as other uses.

34 Claims, 5 Drawing Sheets

METHOD FOR DETECTING NCRNA

This application is a national stage application of international application no. PCT/US2005/013247, filed Apr. 20, 2005, which claims priority to and the benefit of U.S. provisional patent application no. 60/563,877, filed Apr. 20, 2004.

BACKGROUND

The general basis of cancer is the loss of cell growth control mechanisms and the resulting abnormal proliferation of cells. Traditionally, a universal paradigm in oncogenesis is the accumulation of mutations in the coding or regulatory regions of cellular genes such as oncogenes and tumor suppressor genes. These mutations lead to perturbations of the normal cellular signaling processes that govern cellular proliferation and development. However, recent research has revealed a new class of Ranks termed non-coding Ranks (ncRNA) (also referred to as functional RNA, or frank). ncRNAs include a variety of RNA molecules including, but not limited to, miRNA (micron), rena (ribosomal RNA), siRNA (small interfering RNA), snRNA (small nuclear RNA), snmRNA (small non-mRNA), snoRNA (small nucleolar RNA) and stRNA (small temporal RNA). The functions of these ncRNAs are diverse and are still being determined. Many of the ncRNA molecules interact with proteins to form rib nucleoprotein (RNP) complexes.

miRNA has emerged as one of the more intriguing members of the ncRNA class. miRNA has been determined to be important for cellular growth, development and homeostasis and research points to the involvement of these miRNAs in a variety of disease states, such as cancer. miRNAs are short nucleotide transcripts cleaved from a larger hairpin precursor. In certain embodiments, the miRNA are 19-23 nucleotides in length. Research suggests that the Dicer protein and related proteins are involved in the cleavage of the RNA hairpin precursor to form the miRNAs (Hutvagner et al., Science 293: 834-838, 2001; Ketting et al., Gene & Development. 15: 2654-2659, 2001). Many miRNAs, often with highly conserved sequences, are present in the genomes of organisms, such as, but not limited to, Caenorhabditis elegans, Drosophila, rats, mice, and humans (Lagos-Quintata et al., Science 294: 853-858 2001; Lagos-Quintata et al., Curr Biol 12, 735-739, 2002; Lee and Ambros Science 294: 862-86 2001; Mourelatos et al. Gene & Development, 16: 720-7282002; Dostie et al. RNA 9: 180-186, 2003). In some instances, the miRNAs are organized in the genome as clusters, sometimes separated by intervals as short as a few nucleotides.

The roles proposed for miRNAs are diverse. miRNAs are postulated to be involved in regulation of mRNA stability and translation, heterochromatin formation, genome rearrangement, and DNA excision (Baulcombe Science 297:2002-2003, 2002). In *C. elegans*, miRNAs coordinate the translation of heterochromic genes (Banerjee et al., BioEssays, 24: 119-129, 2002). Two *C. elegans* miRNAs, lin-4 and let-7, control developmental timing by forming imperfect base pairing with elements within the 3' UTR of target mRNAs and attenuating their translation (Lee et al., Cell 75:843-854, 1993; Wightman et al., Cell. 75(5):855-62, 1993). A specific miRNA in *Arabidopsis* is known to direct the cleavage of transcripts encoding several putative transcription factors (Llave et al., Science, 297: 2053-2056, 2002). The *Drosophila bantam* gene encodes a miRNA that regulates cell proliferation and the pro-apoptotic gene hid (Brennecke et al., Cell, 113: 25-36, 2003). Evidence supporting the notion that miRNAs are an important class of regulatory molecule is growing.

Given the fundamental biological processes that are regulated by miRNAs and the knowledge that many of these processes are altered in a variety of human conditions, it is important to determine whether miRNAs play a role in these conditions. For example, miRNAs have recently been implicated in carcinogenesis and development and differentiation of numerous cell types.

Metzler et al (Gene Chromosomes Cancer, 39(2): 167-9, 2004) reported recently that mir-155/bic RNA expression is up-regulated significantly in children with Burkitts Lymphoma. Recent studies by Michael et al (Mol Cancer Res. 1(12), 882-91, 2003) has shown that specific miRNAs shown reduced accumulation in colorectal neoplasia. Calin et al (Proc Natl Acad Sci USA., 99(24):15524-9, 2002) found an association between chronic lymphocytic leukemia (CLL) and deletions in a region of chromosome 13, which contains the coding regions for the miRNAs miR-15 and miR-16. They found that these miRNAs are either absent, or down-regulated, in a majority of CLL specimens (~68%). Hemizygous and/or homozygous loss at 13q14 constitute the most frequent chromosomal abnormality in CLL. Deletions at this region also occur in approximately 50% of mantle cell lymphomas, in 16-40% of multiple myelomas, and in 60% of prostate cancers, suggesting the involvement of one or more tumor suppressor genes at this locus. Although several groups have performed detailed genetic analysis, including extensive loss of heterozygosity (LOH) analysis, mutation, and expression studies, no consistent involvement of any of the genes located in the deleted region has been demonstrated. If loss of the 13q14 miRNA R-15 and R-16 locus is key for the genesis of CLL, then these data by Calin et al are consistent with the idea that a miRNA may act as a tumor suppressor.

It is also possible that cancer could result from translocations of oncogene into miRNA loci. One such potential example of this is the translocation of MYC into the miRNA mir-142 loci, which causes an aggressive B cell leukemia due to strong up-regulation of MYC expression (Gauwerky et al., Proc Natl Acad Sci USA 86, 8867-8871, 1989). The MYC gene translocated only 4 nucleotides downstream of the mir-142 3' end, and is likely under control of the upstream miRNA promoter. Alignment of mouse and human mir-142 containing EST sequences indicates ~20 nucleotide conserved sequence element downstream of the mir-142 hairpin, which is lost in the translocation (Lagos-Quintana et al., Curr. Biol. 12:735-739, 2002). It was suggested that the absence of this conserved downstream sequence element in the putative mir-142/MYC fusion prevented the recognition of the transcript as a miRNA precursor to be properly processed, and therefore may have caused accumulation of fusion transcripts and overexpression of MYC. Thus there are multiple avenues for miRNA involvement in disease states, such as cancer, and the identification of miRNAs will likely help us to understand the cooperation of miRNA mechanisms in the biochemical mechanisms underlying the disease states.

Sempere et al. (Genome Biol. 5(3):R13. Epub 2004 Feb. 16, 2004) recently reported the identification of a subset of brain-expressed miRNAs whose expression behaviour is conserved in both mouse and human differentiating neurons. This data suggests that these miRNAs play a role in normal mammalian neuronal development and/or function. Furthermore, Houbaviy (Dev Cell. 5(2):351-8, 2003) identified a group of miRNAs in undifferentiated and differentiated mouse embryonic stem cells, with some of the miRNAs being specifically restricted to stem cells. The repression of these embryonic-specific miRNAs is repressed when the embryonic stem cells beings to differentiate. This suggests a role for miRNAs in the maintenance of the pluripotent cell state and direction of early mammalian development.

Approximately 220 miRNAs have been identified in humans and many of the identified miRNAs have been associated with important biological functions. By bioinformatics approach, Bartel and Burge (2003) estimated that up to 1% of the human genome may code for miRNAs. The roles of miRNA played in normal tissue development and cellular functions are just beginning to be explored. However, discoveries in the ncRNA field are severely hindered by the lack of efficient analytical tools. The timely development of a powerful tool to aid the study of ncRNA, such as miRNA, molecules is therefore needed. The present disclosure provides such an analytical tool for the analysis of ncRNAs. The present disclosure provides methods describing the detection and analysis of miRNAs. However, the methods of the present disclosure may also be applied to other ncRNAs as would be obvious to one of ordinary skill in the art.

DETAILED DESCRIPTION

Prior Art Methods for ncRNA Detection

Figure 1:
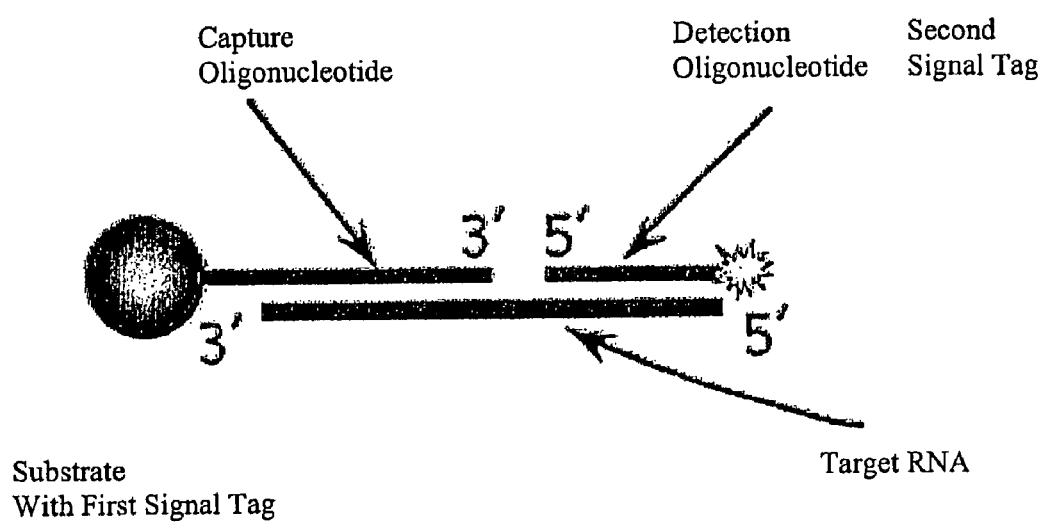
FIG. 1 shows a pictorial representation of one embodiment of the miRNA detection method of the present disclosure. In this embodiment, the capture oligonucleotides are coupled to a solid, internally color-coded microsphere (which serves as the substrate and contains the first signal tag).

The art currently relies on a variety of traditional detection methods to detect ncRNAs. The currently used assays include the use of Northern blots, array based methods and RNAse protection assays. The use of a Northern blots to detect ncRNAs generally requires 15-20 µg of total RNA for an analysis and is used primarily for the study of one particular ncRNA. The total RNA (or RNA enriched by size fractionation) is run on a standard gel and transferred onto membrane. Labeled probe complementary to the RNA species to be detected, such as a radio-labeled probe, is used to hybridize to the desired RNA species for specific detection. This method is time consuming, labor intensive and demands large quantities of total RNA. In addition, one hybridization could only study the expression of one particular ncRNA or a small numbers of ncRNA if the length of the miRNAs was different enough to provide separation. Although the membrane can be striped and reused to study other RNA species, multiple usage of a membrane makes it difficult to compare results acquired between assays.

Krichevsky et al (RNA, 9(10):1274-81, 2003; Erratum in: RNA, 10(3):551. 2004) reported the use of a printed array to study the expression of ncRNA, specifically miRNAs. Trimer oligonucleotides (complementary to the miRNAs to be analyzed) of 54-72 nucleotides in length at final concentration of 7 µM were spotted on the GeneScreen Plus (NEN) membrane. For each experiment, 5-10 µg of miRNA from brain tissue was used as probes. The miRNA probes were labeled with $\gamma^{33}P$ dATP (3000 Ci/mmole) by T4 polynucleotide kinase. The hybridization reaction usually occurs over night and requires extensive washes for optimal specificity. While the printed array method can analyze the expression of multiple miRNAs in one assay, its specificity and sensitivity are limited by sample preparation, probe labeling efficiency, hybridization and washes. Because many miRNAs share large homologous conserved sequences, especially those belong to the same family, the detection specificity of using the printed array is severely limited.

The RNase protection assay is a solution-based hybridization method for ncRNA analysis, such as miRNA analysis. In this method, miRNAs were detected with a 29 nucleotide radiolabeled probe prepared by in vitro transcription (IVT). The probe carries a 10 nucleotide sequence at its 5' end that is not complementary to the miRNA sequence and is cleavable by RNases. After incubation at 42° C. for 15 hours, reactions were treated with RNases A and T1 for at least 30 min at 37° C. Protected fragments were recovered by precipitation and analyzed on a denaturing polyacrylamide gel. The solution hybridization method is 10 times more sensitive than Northern and can detect miRNAs from 1 µg of total RNA. However, it still requires the preparation of radiolabeled IVT probes and the readout step may require that multiple denaturing polyacrylamide gels be run since each gel could differentiate only miRNAs of different sizes.

All three commonly used methods described above are subject to the same set of limitations. Each of the methods is labor intensive as they require labor intensive and time consuming steps such as radioactive labeling of probes, overnight hybridization, denaturing gel electrophoresis, extensive washing steps, x-ray film exposure and image digitalization for quantitative analysis. Furthermore, other than the printed array method, the methods described are limited in the analysis of multiple miRNAs in a simultaneous manner and are not suited for expression profiling analysis. The assay described herein will not require the labor intensive steps described above, such as probe manufactures, and the entire assay can be completed in one hour.

In addition, the methods described above lack the sensitivity to detect small quantities of ncRNA. Usually 10-20 µg total RNA is required to detect a given ncRNA species. At this sensitivity, a laboratory will have to allocate significant resources for sample RNA preparation. As the results in the Examples section below demonstrate, the ncRNA detection method disclosed can detect the expression of RNA species using as little as 50 ng of total RNA.

Finally, the methods described above and currently used in the art lack the specificity required to differentiate between the highly homologous ncRNA species. Many ncRNAs, such as miRNAs, share extensive sequence homology and are classified into families. Often only one nucleotide base differs among the ncRNA family members. Such homology makes it very difficult for Northern blot or array-based methods to differentiate highly conserved ncRNA family members. The use of short LAN spiked oligonucleotides as described herein significantly increases the specificity of detection and makes it possible to detect even a single nucleotide base difference among ncRNA species.

Overview of ncRNA Detection Methodology

The present disclosure describes a method for the efficient detection of ncRNA molecules (which may be referred to herein as a "target RNA"). As used in this specification, ncRNA is meant to define any small RNA molecule and specifically includes, but is not limited to, miRNA, siRNA, and stRNA. In one embodiment, ncRNAs have a length of 5 to 500 nucleotides. In an alternate embodiment, the ncRNAs have a length of 5 to 100 nucleotides. In yet another alternate embodiment, the ncRNAs have a length of 5 to 40 nucleotides. The method of the present disclosure can be used to detect any known or unknown ncRNA molecule, In one embodiment, the disclosed method is used to detect miRNA molecules. For the purpose of exemplifying the method claimed, the disclosed method is used to detect the presence of miRNA molecules. However, the present method is not limited in application to the detection of miRNA molecules only and should be understood to include the detection of any ncRNA molecule.

The detection methods disclosed herein may be used in a variety of applications. In one embodiment, the detection methods disclosed may be used to generate a profile the various ncRNA species present in a sample from a subject. In a specific embodiment, the ncRNA is a miRNA. The unique and novel approach to ncRNA detection as disclosed in the present application allows for the first time the analytical power to profile multiple ncRNA species in an efficient, non-labor intensive method.

In an alternate embodiment, the detection methods disclosed may be used to profile the various ncRNA species present in a given disease or condition, such as but not limited to cancer, to create a ncRNA signature for the disease state or condition. In one approach, a first sample is obtained that is characterized as having a particular disease or condition and the ncRNA profile is determined; a second sample is obtained that is characterized as being free from a particular disease state or condition and the ncRNA profile is determined. Multiple first and second samples may be obtained if desired. The ncRNA profiles from the first and second samples are compared, and the ncRNAs that show differences (such as increased expression or decreased expression) are noted. These ncRNA species constitute the ncRNA signature for the disease or condition. In a specific embodiment, the ncRNA is a miRNA. The first and second samples may be obtained from the same subject or from separate subjects. In one embodiment, the first and second samples are obtained from the same subject. In a particular application, the ncRNA signature may be correlated with a characteristic of the disease or condition by selecting first and/or second samples that exhibit the desired characteristics. The characteristics of the disease or condition include, but are not limited to, the state of advancement/progression of the disease or condition, and the responsiveness of the disease or condition to a particular medication, treatment regimen or therapy. For example, assume the disease or condition is breast cancer. The first sample can be a sample(s) from breast tumors that are responsive to drug A; the second sample(s) can be normal breast tissue. The ncRNA signature can be determined. The process can be repeated as above, except that the first sample(s) are from breast tumors that are responsive to drug B. By comparing the ncRNA profiles obtained, ncRNA signatures can be obtained that are correlated with drug responsiveness.

The ncRNA signature for a disease or condition may be utilized in a number of ways. The ncRNA profile from a subject can be compared to the ncRNA signature for the given disease or condition. In this manner the comparison can be used to classify a subject as having the particular disease or condition or being at risk for the particular disease state of condition. In addition, the comparison may be used to determine the potential responsiveness to a medication, treatment regimen or therapy. Furthermore, the comparison may be used to determine the state of progression of the disease or condition in the subject. In addition, the ncRNA signature for the disease or condition may be used to monitor the progression of the disease or condition. Also, the ncRNA signature for a disease or condition may be used to monitor the efficacy of a medication, treatment regimen or therapy.

In yet another embodiment, the detection methods disclosed may be used to identify potential drug targets for the treatment of a disease or condition. As discussed above, ncRNA signatures for a particular disease or condition may be created. By determining the identity of the ncRNA species that characterize a particular disease or condition, the identity of molecular targets involved in the molecular pathways responsible for the disease state or condition may be identified. These molecular targets may provide novel therapeutic candidates for drug development for the treatment and/or prevention of the disease or condition. In such a method, the ncRNA signature for a disease or condition is obtained as described above. The ncRNA molecules that characterize the disease or condition are noted. The identity of the ncRNA molecules is used to determine the molecular targets involved in the molecular pathways of the disease or condition. In a specific embodiment, the ncRNA is a miRNA.

The detection method described may use modified nucleotides to enhance the Tm of the capture and detection oligonucleotides with their complementary sequences on the target RNA. Various modified nucleotides sufficient for this purpose are known in the art. In one embodiment, the modified nucleotides are locked nucleic acids, or LNA™. In an alternate embodiment the modified nucleotides may comprise peptide nucleic acids (PNA). Other modified nucleotides may be used as are known in the art or as are developed in the art. The use of modified nucleotides to enhance Tm in the capture and detection oligonucleotides described below provides for increased specificity and sensitivity of target RNA detection. Furthermore, through the incorporation of one or modified nucleotides into the capture and detection oligonucleotides of the disclosure (as described in more detail below), the Tm of binding of the capture and detection oligonucleotides to their complementary sequences on the target RNA can be engineered to be about the same. As used herein, a LNA base or nucleotide, refers to a bicyclic nucleic acid where a ribo-nucleoside is linked between the 2'-oxygen and the 4'-carbon atoms with a methylene unit. Oligonucleotides containing LNA nucleotides exhibit unprecedented thermal stabilities towards complementary DNA and RNA. On average, each modified (spiked) LNA nucleotide will increase the Tm for a LNA:RNA hybrids by 7.3° C. The high binding affinity of LNA containing oligonucleotides allows for the use of shorter oligonucleotide sequences for use as probes and makes LNA containing oligonucleotides excellent probes for mismatch discrimination.

LNA oligonucleotides can be synthesized by standard phosphoramidite chemistry using DNA-synthesizers. LNA can be mixed with DNA, RNA as well as other nucleic acid analogs. It can be synthesized with biotin, Cy dyes or other dyes as is known in the art. LNA containing oligonucleotides are water-soluble and basepair with DNA and RNA with exceptionally high thermal stability. Exiqon (Demark) has developed software for predicting the melting behavior and Tm of LNA containing oligonucleotides and for assisting in the design of LNA containing oligonucleotides. Furthermore, since LNA containing oligonucleotides can hybridize with both RNA and DNA molecules, any type of nucleic acid can be detected using the method described herein. When a double stranded RNA or DNA molecule is to be detected, it may be required to denature the double stranded molecules before the hybridization steps described herein.

General Description of ncRNA Detection Methodology

The detection method comprises the use of a capture oligonucleotide and a detection oligonucleotide. The capture oligonucleotide comprises a first signal generator to produce a first detectable signal and the detection oligonucleotide comprises a second signal generator to produce a second detectable signal. The first and second detectable signals may be any signal that can be detected using commercially available devices. The first and second detectable signals may be an emission of a given wavelength (such as but not limited to light to produce an optical signature), a change in electrical properties such as conductivity, or a change in the electromagnetic or chemical properties. In one embodiment, the first and second detectable signals are optical signatures. In one embodiment, the optical signature is generated using a chromophore, a flourophore or any other reagent capable of generating an optical signature. A variety of optical signatures may be created by mixing different chromophores or flourophores or using different concentrations (intensities) of the same. The first and second detectable signals are capable of being detected in the presence of one another. The first and second detectable signals may be associated directly or indirectly with the capture oligonucleotide and the detection oligonucleotide, respectively. In one embodiment, the first detectable signal on the capture oligonucleotide is a microsphere capable of generating said first detectable signal. In a specific application, the microsphere is a color-coded microsphere, such as the microspheres manufactured by Luminex (Austin, Tex.). The Luminex technology and related technologies are described in the art and in U.S. Pat. Nos. 6,524,473, 6,514,295, 6,449,562, 6,411,904, 6,366,354, 6,268,222, 6,139,800, 6,057,107, 6,046,807 and 5,736,330. The capture oligonucleotide may be coupled to the microsphere by covalent or non-covalent means. The capture and detection oligonucleotides are specific to a target RNA of interest (such as a miRNA), allowing the detection of any known target RNA species with the appropriate design of the capture and detection oligonucleotides. Each of the components of the method is described in more detail below.

Any target RNA species may be targeted for detection. The only requirement is that at least a portion of the sequence of the target RNA is known. The entire sequence of the target RNA need not be know, so long as the known sequence is of a sufficient length to hybridize to the detection and capture oligonucleotides as described below. In one embodiment, the entire sequence of the target RNA is known.

For each target RNA species targeted for detection, a specific capture oligonucleotide is designed. The first detectable signal generated by the first signal generator is used to identify the capture oligonucleotide throughout the method, and therefore, to determine the identity of the target RNA bound by the capture oligonucleotide. In one embodiment, the first detectable signal may comprise an optical signature. In one embodiment, when the first detectable signal is an optical signature, the optical signature may be contained in a microsphere. In alternate embodiment, the first detectable signal may be a pre-determined position, such as may be the case when the capture oligonucleotide is attached to a pre-printed array or the like.

The capture oligonucleotide comprises a short nucleic acid sequence complementary to at least a portion of the sequence of the target RNA species to be detected (termed the "capture sequence"). In one embodiment, the length of the capture oligonucleotide is from 6 to 14 nucleotides. In a further embodiment, the length of the capture oligonucleotide is 8-12 nucleotides. In yet another embodiment, the length of the capture oligonucleotide is 12 nucleotides. The length of the capture sequence corresponds to the length of the capture oligonucleotide. The capture oligonucleotide may contain one or more modified nucleotides, such as LNA nucleotides, to enhance binding specificity and binding efficiency. In one embodiment, at least 1 nucleotide bases of the capture oligonucleotide is a modified nucleotide. In an alternate embodiment, at least 2-4 nucleotide bases of the capture oligonucleotide are modified nucleotides. In yet another alternate embodiment, at least 5 nucleotide bases of the capture oligonucleotide are modified nucleotides. The modified nucleotides may be spaced apart within the nucleotide sequence of the capture oligonucleotide, may be contiguous in the nucleotide sequence of the capture oligonucleotide, or a combination of the foregoing. In yet another embodiment, the capture oligonucleotide does not contain any modified nucleotides. In certain cases where the GC content of the of the capture sequence is high enough, the Tm of a capture oligonucleotide having a length as described above will be sufficient to achieve the specificity and sensitivity of hybridization.

In one embodiment, the nucleotide sequence of the capture oligonucleotide is 100% complementary to the nucleotide sequence of the capture sequence of the target RNA species to be detected. In an alternate embodiment, the nucleotide sequence of the capture oligonucleotide contains at least one mismatched base as compared to the nucleotide sequence of the capture sequence of the target RNA species to be detected.

The capture oligonucleotide may further comprise a spacer sequence to allow the efficient attachment to the substrate. The spacer sequence is not be complementary to the capture sequence and may be comprised of a nucleic acid component, a non-nucleic acid component or a combination of nucleic acid and non-nucleic acid components. In one embodiment, the spacer is a nucleic acid sequence that is not complementary to a sequence to be detected. In an alternate embodiment, the spacer is a carbon based spacer of 6-15 carbons in length. The capture sequence may be located at any convenient position on the target RNA molecule to be detected. In one embodiment, the capture sequence is located toward the 5' end of the target RNA molecule. The position toward the 5' end of the target RNA molecule may be defined such that the capture sequence contains the 5' most nucleotide of the target RNA molecule or may be defined such that the capture sequence omits one or more of the 5' most nucleotides of the target RNA molecule. In an alternate embodiment, the capture sequence is located at the 3' end of the target RNA. The position toward the 3' end of the target RNA molecule may be defined such that the capture sequence contains the 3' most nucleotide of the target RNA molecule or may be defined such that the capture sequence omits one or more of the 3' most nucleotides of the target RNA molecule. The length of the capture oligonucleotide will correspond to the length of the capture sequence, as discussed above. In yet another alternate embodiment, the capture sequence is located in the middle portion of the target RNA molecule.

The detection oligonucleotide comprises a short nucleotide sequence complementary to at least a portion of the nucleotide sequence (termed the "detection sequence") of the target RNA species to be detected. In one embodiment, the length of the detection oligonucleotide is from 6 to 14 nucleotides. In a further embodiment, the length of the capture oligonucleotide is 8-12 nucleotides. In yet another embodiment, the length of the capture oligonucleotide is 10 nucleotides. The detection oligonucleotide may contain one or more modified nucleotides, such as LNA nucleotides, to enhance binding specificity and binding efficiency. In one embodiment, at least 1 nucleotide base of the detection oligonucleotide is a modified nucleotide. In an alternate embodiment, at least 2-4 nucleotide bases of the detection oligonucleotide are modified nucleotides. In yet another alternate embodiment, at least 5 nucleotide bases of the detection oligonucleotide are modified nucleotides. The modified nucleotides may be spaced apart within the nucleotide sequence of the detection oligonucleotide, may be contiguous in the nucleotide sequence of the detection oligonucleotide, or a combination of the foregoing. In yet another embodiment, the detection oligonucleotide does not contain any modified nucleotides. In certain cases where the GC content of the of the detection sequence is high enough, the Tm of a detection oligonucleotide having a length as described above will be sufficient to achieve the specificity and sensitivity of hybridization.

One end of the detection oligonucleotide comprises a second signal generator to produce a second detectable signal. The second detectable signal is detectable in the presence of the first detectable signal. The simultaneous detection of the first and second detectable signals is required to generate a positive identification of a given target RNA. The second detectable signal may comprise an optical signature. The second signal generator may be directly attached to the detection oligonucleotide. Alternatively, the second signal generator may be indirectly attached to the detection oligonucleotide, such as through the use of complementary binding pairs. Complementary binding pairs are meant to refer to binding pairs such as biotin/streptavidin, biotin/avidin and other such complexes as may be known in the art. The complementary binding pairs may also include chemical moieties, organic moieties or complementary amino acid or nucleic acid sequences. A variety of optical signatures may be created by mixing different chromophores or flourophores or using different concentrations (intensities) of the same.

In one embodiment, the nucleotide sequence of the detection oligonucleotide is 100% complementary to the detection sequence of the target RNA species to be detected. In an alternate embodiment, the nucleotide sequence of the detection oligonucleotide contains at least one mismatched base as compared to the nucleotide sequence of the detection sequence of the target RNA species to be detected. The detection sequence may be located at any convenient position on the target RNA molecule. In one embodiment, the detection sequence is located toward the 5' end of the target RNA molecule. The position toward the 5' end of the target RNA molecule may be defined such that the detection sequence contains the 5' most nucleotide of the target RNA molecule or may be defined such that the detection sequence omits one or more of the 5' most nucleotides of the target RNA molecule. In an alternate embodiment, the detection sequence is located at the 3' end of the target RNA. The position toward the 3' end of the target RNA molecule may be defined such that the detection sequence contains the 3' most nucleotide of the target RNA molecule or may be defined such that the detection sequence omits one or more of the 3' most nucleotides of the target RNA molecule. The length of the detection sequence will correspond to the length of the detection oligonucleotide selected, as discussed above. In yet another alternate embodiment, the detection sequence may be located in the middle portion of the target RNA molecule.

In one embodiment, the detection sequence is selected so that there is no overlap between the detection sequence and the capture sequence. Therefore, in one embodiment if the capture sequence is located toward the 5' end of the target RNA molecule, the detection sequence is located toward the 3' end of the target RNA molecule. Likewise, in an alternate embodiment, if the capture sequence is located toward the 3' end of the target RNA molecule, the detection sequence is located toward the 5' end of the target RNA molecule.

In one embodiment, the capture oligonucleotides and the detection oligonucleotides have substantially the same Tm on binding to the capture and detection sequences, respectively. By substantially the same Tm on binding it is meant that the Tm for binding of the capture oligonucleotide to the capture sequence and the binding of the detection oligonucleotide to the detection sequence differ by 1-5 degrees Celsius. In one embodiment, the Tms differ by 1-3 degrees Celsius. In an alternate embodiment, the Tms differ by 1-2 degrees Celsius. In still another embodiment, the Tms differ by 1 degree Celsius. By having the Tm values for binding between the capture oligonucleotide and the capture sequence and the detection oligonucleotide and the detection sequence being substantially the same, the sensitivity of the detection reaction can be significantly increased without sacrificing specificity of detection. Exiqon (Demark) has developed software for predicting the melting behavior and Tm of LNA containing oligonucleotides and for assisting in the design of LNA containing oligonucleotides. In one embodiment, the length and composition (including the incorporation of modified nucleotides, if used) of the capture and detection oligonucleotides are selected so that the capture and detection oligonucleotides will have similar Tm values for hybridization to the capture sequences and detection sequences, respectively of the target RNA.

In certain embodiments, it will be advantageous to detect a family of related target RNA species in a single reaction. Such family members often share high homology over significant lengths of the target RNA (Examples are provided below for the detection of related miRNA species). Where the detection of a family of related target RNA species is desired, the capture oligonucleotide or the detection oligonucleotide may have the same nucleotide sequence for one or more of the related target RNA species to be detected (see Table 1 in Example 1). In certain other embodiments where the target RNA species to be detected do not share homology, the capture oligonucleotide and/or the detection oligonucleotide may have different nucleotide sequences for each target RNA.

The present method envisions that more than one target RNAs may be detected in a single detection reaction. Therefore, a plurality of capture oligonucleotides and detection oligonucleotides can be used to recognize capture sequences and detection sequences, respectively, on a plurality of target RNA species in the same detection reaction. Where multiple target RNA species are to be detected in a single detection reaction, the lengths of the capture oligonucleotides and/or detection oligonucleotides may be different or may be the same, the number of modified nucleotides incorporated into the nucleotide sequence of the capture oligonucleotide and/or defection oligonucleotides may be different or the same, and the location of the capture sequence and/or detection sequences on the target RNA species to be detected may be different or the same.

In the detection method disclosed, sample RNA is obtained from a source. The sample RNA contains at least one target RNA species to be analyzed. The source may be any source containing RNA. The source may be human, plant, animal (including eukaryotic and prokaryotic organisms) or viral. The sample RNA may be taken from a tissue, blood, saliva or other excretion. The source may be cell line derived from a human, plant or animal. In one embodiment, more than one sample may be obtained from the source. In this embodiment, one sample may be taken from a tissue characterized as having a disease and the one sample may be taken from a tissue characterized as not having the disease. Methods for isolating RNA are known in the art. The sample RNA may be total RNA. Alternatively, the sample RNA may be fractionated, purified or partially purified. In one embodiment, the sample RNA is fractionated according to size to remove higher molecular weight RNA components. The fractionation may be accomplished by any method known in the art, such as chromatographic methods. In another alternate embodiment, whole cell lysate may be used without requiring purification of RNA.

The detection method may be carried out in a variety of embodiments. In one embodiment, the sample RNA containing the target RNA(s) to be detected is mixed with and incubated with the capture oligonucleotides and the detection oligonucleotides to allow the simultaneous hybridization between the capture oligonucleotide and the capture sequence and the detection oligonucleotide and the detection sequence on the target RNA species to be detected. The product of this reaction is a complex (the "detection complex") consisting of the capture oligonucleotide and the detection oligonucleotide bound to the target RNA species via the capture and detection sequences respectively. In an alternate embodiment, the sample RNA containing the target RNA(s) to be detected is mixed with and incubated with the capture oligonucleotides to allow the hybridization between the capture oligonucleotide and the capture sequence on the target RNA species to be detected. A wash step may be preformed. Subsequently, the detection oligonucleotides are incubated with the capture oligonucleotide/target RNA complex to allow hybridization between the detection oligonucleotide and the detection sequence on the target RNA species to be detected to form the detection complex.

A variety of hybridization conditions may be used. In one embodiment, the hybridization reactions take place in solution (meaning that the capture and detection oligonucleotide sequences and the target RNA are free in solution) in the presence of a hybridization buffer. IN an alternate embodiment, at least one of the detection or capture oligonucleotides are bound to a substrates, such as a chip or other solid support. In one embodiment, the hybridization conditions comprise incubation for an appropriate period of time at an appropriate temperature (such as at 52° C. for 1 hour) in 1×TMAC buffer (3M TMAC, 0.1% Sarkosyl, 50 mM Tris-HCl pH 8.0, 4 mM EDTA pH 8.0). TMAC buffer offers the advantage that hybridization properties are determined primarily by the oligonucleotide length and is independent of base composition, so that single-base mismatches are easily detected under a standard set of conditions. However, other hybridization buffers may be used. In alternate embodiments, the hybridization buffer may be 1×SSCT (1×SSC containing 0.05% (v/v) Tween 20) or of sodium phosphate buffer (50 mmol/L sodium phosphate buffer, pH 7.0, 0.1 mL/100 mL Tween 20) or other hybridization buffers known in the art. In addition, hybridization times (see Table 4 in Example 1) and hybridization temperatures may be varied as discussed below and as is known in the art. For example, the hybridization time may be decreased to 10 minutes or less (see Table 5 in Example 1 below). A 10 minute hybridization time produced a signal that was approximately 70% of that observed during a 1 hour hybridization period. Therefore, the hybridization times may be varied as would be obvious to one of skill in the art depending on the required sensitivity of the detection reaction.

In the embodiment, where the capture oligonucleotides are conjugated to a microsphere or a substrate (such as a chip or other solid support ), the density of the capture oligonucleotides on the microsphere or substrate may also be varied. The density of the capture oligonucleotide on the microsphere or substrate may influence capture efficiency. The density of the capture oligonucleotides may range from $10^4$ to $10^9$ capture oligonucleotides/microsphere or substrate. In one embodiment, density of the capture oligonucleotides may range from $10^6$ to $10^8$. For shorter target RNAs, such as miRNAs, the density of the capture oligonucleotide will be less of a concern than for larger nucleic acid molecules as the smaller RNA molecules may have easier access to the capture oligonucleotides conjugated to the substrate. Likewise, the concentration of the detecting oligonucleotides may be varied. In one embodiment, the detection oligonucleotides are used in an excess as compared to the miRNA target specie(s). In the experiments described in the Examples section below, the detection oligonucleotides are used at a concentration of 10 pmol. However, other concentrations may be used as would be obvious to those skilled in the art. In general, the concentration of detection oligonucleotides is selected so as to minimize background caused by excess detection oligonucleotide.

The concentration of the capture and detection oligonucleotides may be varied in order to increase or decrease the sensitivity of the detection reaction. For example, if it is desired to detect a plurality of target RNAs, one or more of these target RNAs may be present in significantly different concentrations. In order to keep the signals detected in the linear range, it may be desirable to decrease the signal generated for a particular target RNA by decreasing the concentration of the appropriate capture and detection oligonucleotides. Likewise, it may be desirable to increase the signal for a particular target RNA. In this case the concentration of capture and detection oligonucleotides for the appropriate target RNA may be increased.

After hybridization between a target RNA to be detected and the capture and detection oligonucleotides, the resulting detection complex is centrifuged to pellet the detection complex. In this manner, excess detection oligonucleotide and RNA components may be removed. The excess liquid is removed. Wash steps using commonly known washing buffers may be performed if desired. However, the results in the Example section below were conducted without wash steps. The detection complex may then be subject to detection. Reagents required for the visualization of the first and/or second detectable signals may be added prior to the detection reaction if required. In one embodiment, a fluorescent moiety (such as PE) is linked to one part of a complementary binding pair (such as streptavidin) and added for binding to the other component of the complementary binding pair on the detection oligonucleotide (such as biotin). The detection reaction detects the first detectable signal and the second detectable signal. Therefore, the identity of the capture oligonucleotide is given by the detectable signal (and therefore, the identity of the target RNA species bound to the capture oligonucleotide) and the presence of a target RNA in the detection complex is determined by the second detectable signal associated with the detection oligonucleotide. The second detectable signal may be the same for each detection oligonucleotide. The method of detection of the first and second signal tags will vary depending on the nature of said tags as is known in the art. In one embodiment, first and second detectable signals are fluorescent signals and the detection method involves an automated, high throughput detection platform.

In a more specific embodiment, the first detectable signal is a internally color-coded microsphere utilizing the X-Map technology developed by Luminex with the internally color-coded microsphere serving as the first detectable signal, the second detectable signal is a fluorescent streptavidin-PE label and the automated, high throughput detection platform is the Luminex platform (such as but not limited to the Luminex 100 instrument). At least 100 target RNA can be analyzed in a single assay. By performing multiple assays, the number of target RNAs to be analyzed is infinite.

The presence of target RNA in the sample can be measured as a function of the fluorescent intensity. In this embodiment, the reaction mixture is injected into the Luminex platform which uses microfluidics to align the microspheres in single file where lasers illuminate the colors inside the microsphere (i.e., the first detectable signal) and on the surface of each microsphere (i.e. the second detectable signal). For each color-coded microsphere, the Luminex platform records 100 separate readings to take an average for data reporting. From a statistical point of view, that is 100 data points per target to be detected. Advanced optics captures the color signals. Finally, digital signal processing translates the signals into real-time, quantitative data for each reaction.

Appropriate controls may also be added to the detection method. Many types of internal and external controls may be employed as is known in the art. An internal control will allow an investigator to normalize and compare data regarding target RNA levels at different time points (such as before and after a treatment protocol) and to normalize the variations introduced by the sample handling process. The internal control may be selected to mimic the characteristics of the target RNA to be detected. In one embodiment, the internal control is 5S or 5.8S rRNA. Both 5S and 5.8S rRNA are ubiquitously expressed and are small RNA molecules. Capture and detection oligonucleotides will be prepared for the internal controls in the same manner as for target RNA molecules. Furthermore, if the expression level for the internal control is too high to be compared with the target RNA to be detected, the system may be modified to make the detection of the internal control less sensitive (i.e. by adding more internal control-specific beads to the reaction, by decreasing the number of capture oligonucleotides specific for the internal control/substrate or by adding unlabeled, un-conjugated capture oligonucleotides to the reaction mixture).

External controls (standards) may also be included. The external control is used to normalize data and cancel out variations introduced by the Luminex machine and the detection system. In one embodiment, four to five specific oligonucleotides will be coupled to different substrate molecules (such as different color-coded microspheres). The oligonucleotides either contain the second signal tag or are able to bind the second signal tag as discussed above. Different amounts of each oligonucleotide will be added for different standards. For example, for Standard A (StdA), 0.1 fmol of biotin labeled probe will be used; for StdB, 1 fmol; for StdC, 10 fmol: and for StdD, 100 fmol. The mean fluorescent intensity of each standard can be acquired, along with all the target RNA molecules to be detected. The relative concentration of the standards, as well as the target RNAs, can be measured.

The results described in the Examples below show that the method disclosed is a very efficient tool for the detection of small target RNA molecules. The method described combines the use of a high throughput detection platform with the enhanced hybridization specificity and sensitivity of modified nucleotides. With the appropriate design of the capture and detection oligonucleotides, multiple target RNA molecules can be studied in one experiment. As a result, the expression pattern or profile of a number of target RNA molecules can be studied. Compared to existing methods, the present detection method disclosed is more about 100 times more sensitive than routinely used Northern blot method. Only 50-100 ng of total RNA is required for a multiplexed analysis. Furthermore, the present detection method disclosed is more specific than existing methods as a result of the use of modified oligonucleotides and liquid phase hybridization format. The present detection method disclosed is also easy to use, requires no labeling of oligonucleotides or sample nucleotide sequences, no amplification of the target RNA molecules and can be completed in as little as 1 hour.

DEFINITIONS

The terms "prevention", "prevent", "preventing", "suppression", "suppress" and "suppressing" as used herein refer to a course of action (such as administering a compound or pharmaceutical composition) initiated prior to the onset of a clinical symptom of a disease state or condition so as to prevent or reduce a clinical manifestation of the disease state or condition. Such preventing and suppressing need not be absolute to be useful.

The terms "treatment", "treat" and "treating" as used herein refers a course of action (such as administering a compound or pharmaceutical composition) initiated after the onset of a clinical symptom of a disease state or condition so as to eliminate or reduce a clinical manifestation of the disease state or condition. Such treating need not be absolute to be useful.

The term "in need of treatment" as used herein refers to a judgment made by a caregiver that a patient requires or will benefit from treatment. This judgment is made based on a variety of factors that are in the realm of a caregiver's expertise, but that includes the knowledge that the patient is ill, or will be ill, as the result of a condition that is treatable by a method or compound of the disclosure.

The term diagnosing as used herein refers to a judgment made by a caregiver that a patient has a specific disease or condition. This judgment is made based on a variety of factors that are in the realm of a caregiver's expertise and may include the use of the methods disclosed herein.

The term "in need of prevention" as used herein refers to a judgment made by a caregiver that a patient requires or will benefit from prevention. This judgment is made based on a variety of factors that are in the realm of a caregiver's expertise, but that includes the knowledge that the patient will be ill or may become ill, as the result of a condition that is preventable by a method or compound of the disclosure.

The term "individual", "subject" or "patient" as used herein refers to any animal, including mammals, such as mice, rats, other rodents, rabbits, dogs, cats, swine, cattle, sheep, horses, or primates, and humans. The term may specify male or female or both, or exclude male or female.

EXAMPLES

Example 1

Detection of Synthetic miRNA Molecules

The methods of the present disclosure were used to analyze 4 closely related ncRNAs, in this example the miRNAs Let-7a, Let-7b, Let-7c, and Let-7g (the sequence of each miRNA is shown in Table 1 along with relevant SEQ ID NOS.). The Let-7a, Let-7b, Let-7c, and Let-7g miRNAs belong to a conserved miRNA family and the 10 nucleotides on the 5' end of each miRNA are conserved. There are minor sequence differences at the 3' end of the miRNAs.

The Let-7a, Let-7b, Let-7c, and Let-7g miRNAs were synthesized by MWG (High Point, N.C.) and their sequences confirmed. The LNA spiked capture oligonucleotides and detection oligonucleotides for Let-7a, Let-7b, Let-7c, and Let-7g were prepared by Phoenix Biotechnologies (Huntsville, Ala.). The sequences of capture and detection oligonucleotides used for each miRNA are also given in Table 1 along with relevant SEQ ID NOS. The capital letters in the respective sequences indicates a LNA base. It should be noted that the nucleotide sequences indicated for the capture oligonucleotides can be modified by adding a spacer group, said spacer group being a carbon based linker (such as, but not limited to, a C6 0r a C12 linker), a nucleotide sequence (such as, but not limited to, aacgcgtata and tacgcgtata, SEQ ID NOS. 94 and 95), or a combination of the foregoing. In one embodiment, the C6 and C12 linkers are used in combination with the nucleotide sequences disclosed in the previous sentence. The predicted Tm for the capture oligonucleotide/capture sequence and the detection oligonucleotide/detection can be predicted. The Tms for the complexes were selected to be substantially equivalent through the use of a computer program available from Exiqon (Demark). Color-coded microspheres were purchased form Luminex Corporation (Austin, Tex.).

In this example, the capture oligonucleotides were designed to hybridize to the 3' end of the desired target miRNAs and the detection oligonucleotides were designed to hybridize to the 5' end of the desired target miRNAs. In this example, the detection oligonucleotides were labeled with a biotin tag at their 3' end to allow interaction with the second detectable signal (which was conjugated to a streptavidin group). Furthermore, a C12 linker sequence was added to the 5' end of each capture oligonucleotide to allow for coupling of the detection oligonucleotides to the microspheres The first detectable signal). The capture oligonucleotides were coupled to the microspheres using the manufacturer's recommended protocol as described below in the Methods.

The detection methodology used in this example is as follows. Sample RNA, in this example the synthetically produced Let-7a, Let-7b, Let-7c and Let-7g miRNAs, is added to 1×TMAC buffer (3M TMAC, 0.1% Sarkosyl, 50 mM Tris-HCl pH 8.0, 4 mM EDTA pH 8.0) at various concentrations as indicated in the tables below. To this reaction tube was added capture oligonucleotides coupled to Luminex microspheres and detection oligonucleotides for each miRNA species to be detected as shown in Table 1 specific. Equal numbers of microspheres (3000) coupled to capture oligonucleotides were added, with approximately $10^6$ to $10^8$ capture oligonucleotides per microsphere (the total concentration of capture oligonucleotide was approximately 0.5 pmol). The detection oligonucleotides were each added at concentration of 10 pmol. The mixture was incubated at 52° C. for 1 hour, or the times indicated below, in 1×TMAC buffer to allow hybridization between the sequences of the capture oligonucleotides and their respective capture sequences and the detection oligonucleotides and their respective capture sequences. After the 1 hour hybridization, the mixture was centrifuged at 15,000 RPM for 2 minutes (room temperature) to pellet the detection complex. The excess liquid was aspirated and 60 µl of diluted straptavidin-PE conjugate was added. The streptavidin-PE conjugate was incubated with the detection complex for 10 minutes at 52° C. to allow binding of the streptavidin-PE conjugate to the biotin tag on the detection oligonucleotides. At the end of the incubation, the mixture was read on a Luminex 100 platform. The entire detection reaction as described can be completed in 90 minutes. As discussed above, the conditions described can be modified.

Tables 2-5 show the specificity and sensitivity of the miRNA detection method disclosed. The columns in Tables 2-5 represent the particular capture and detection oligonucleotide added to the reaction mixture to detect a specific target RNA (indicated as Let-7a, Let-7b, Let-7c and Let-7g). The rows in Tables 2-5 indicates the specific target RNA added to the reaction mixture and the concentration of the target RNA. (each row represents an individual detection reaction). The sequences of each capture and detection oligonucleotide and the synthetic miRNAs are shown in Table 1. The row indicated as "no template" indicates no synthetic miRNA (the target RNA) was added to the reaction and serves as a negative control and background reading. To normalize the data, a percentage value of the signal for a target miRNA is calculated by dividing the specific signal obtained for a particular target miRNA reaction by the total signal from that sample (termed a "normalization ratio"). Those signals greater than 35% of the total signal are highlighted.

In the results shown in Table 2, Let-7a, Let-7b, Let-7c and Let-7g synthetic miRNAs were added at 100, 80, 60, and 40 fmol each. The detection oligonucleotides were each added at a concentration of 10 pmol. In rows 2-5, 100 fmol of Let-7a, Let-7b, Let-7c, and Let-7g synthetic miRNAs were added; rows 6-9, 80 fmol of Let-7a, Let-7b, Let-7c, and Let-7g synthetic miRNAs were added; rows 10-13, 60 fmol of Let-7a, Let-7b, Let-7c, and Let-7g synthetic miRNAs were added; and rows 14-17, 40 fmol of Let-7a, Let-7b, Let-7c, and Let-7g synthetic miRNAs were added. As can be seen in Table 2, the detection of each miRNA species was very specific, with 60% to 91% of the signal detected in a reaction being from the specific target miRNA to be detected. The negative control/background reactions were minimal as shown in row 1 of Table 2.

At 40 fmol concentration of the target miRNA species, sensitive and specific detection is observed. For Let-7a—81% of the signal detected in the sample was from the specific target miRNA to be detected. For Let-7b and Let-7c, 76% of the signal detected in the sample was from the specific target miRNA to be detected. For Let-7g, 91% of the signal detected in the sample was from the specific target miRNA to be detected. This sensitive and specific detection is observed despite the strong sequence homology of the miRNA species detected in the reaction. The sequence of Let-7b and Let-7c differ by only 1 nucleotide. The sequence of Let-7b and Let-7a differ by two nucleotides. The sequence of Let-7b and Let-7g differ by 5 nucleotides.

The data described for the 40 fmol miRNA concentration is indicative of the data obtained at the other miRNA concentrations as can be seen in Table 2. The data in Table 2 indicates that by decreasing the concentration of the miRNA target, specificity was increased slightly.

Table 3 shows the results of the detection assay where the miRNA targets are used concentrations of 10, 1 and 0.1 fmol. The results shown in Table 3 mirror those shown in Table 2, indicating that detection specificity can be maintained at miRNA concentrations as low as 0.1 fmol. At 0.1 fmol, for Let-7a, Let-7b, Let-7c and Let-7g, 70%, 81%, 77% and 91%, respectively, of the signal detected in each sample were from the specific target miRNA to be detected.

Table 4 shows the effect of varying the hybridization time of the detection oligonucleotides coupled to the microspheres and the capture oligonucleotides with the miRNAs to be detected. In the results shown in Tables 2 and 3, a 1 hour hybridization time was used. In table 4, incubation times of 10 minutes, 30 minutes and 60 minutes were compared. The concentration of the Let-7a, Let-7b, Let-7c and Let-7g target miRNAs used in this experiment was 50 fmol. As can be seen in table 4, decreasing the hybridization time to 10 minutes still resulted in good specificity and sensitivity. The signals detected using the 10 minute hybridization reaction were approximately 70% of the signal obtained during the 1 hour hybridization.

To verify the repeatability of the detection method, samples were processed in triplicate as described above and the results compared. In this experiment, the concentration of the Let-7a, Let-7b, Let-7c and Let-7g target miRNAs was 50 fmol, the detection oligonucleotides were used at a concentration of 10 pmol and a hybridization time of 60 minutes was used. Table 5 shows the results of the detection. As can be observed, the repeatability of the detection method is excellent with an average CV of only 1.7%.

Example 2 miRNA Profiling of Total RNA from Rat Brain

In this example, the ability of the detection method disclosed to detect various miRNAs present in a natural RNA source was examined. In this example, the RNA source was a rat brain. The detection method used in the experiments described in Example 2 was identical to the method used in Example 1, with the exception that the sample RNA was RNA extracted from rat brain by standard methodologies rather than synthetically produced miRNAs. The sequence of the capture and detection oligonucleotides is that shown in Table 1. The sample RNA was either column purified to enrich the percentage of small mRNAs or used as total RNA without purification steps. As above, the columns in Tables 6-7 represent the particular capture and detection oligonucleotides added to the reaction mixture specific for a given target RNA (indicated as Let-7a, Let-7b, Let-7c and Let-7g). The rows in Tables 6-7 indicates sample RNA added to the reaction mixture and the concentration at which sample RNA was added (each row represents an individual detection reaction). The results of the detection are shown in Tables 6 and 7.

The results in Table 6 show that the detection method disclosed is able to detect the presence of miRNA molecules from size fractionated (indicated as purified) and total RNA. Row 1 is a negative control (no RNA added to the reaction). Rows 2-4 indicate total RNA at 4 µg, 400 ng and 40 ng, respectively, was added to the reaction mixture. In rows 5-7, column purified RNA enriched in small RNAs at 400 ng, 40 ng and 4 ng, respectively, was added to the reaction mixture. Rows 8-11 were positive controls where 5 fmol of specific target synthetic miRNA was added to the reaction mixture. The detection oligonucleotides were added at 10 pmol. The results in Table 6 show that miRNAs could be detected in RNA preparations enriched in small RNAs as well as in total RNA (without enrichment for small RNAs). With the increased sensitivity of the detection method disclosed, enrichment of the RNA from the source is not required.

To explore the limits of sensitivity of the miRNA detection method, the total RNA preparations were diluted to concentrations of 1600, 800, 400, 200, 100 and 50 ng in rows 1-6 respectively. As before, detection oligonucleotide was added at a concentration of 10 pmol. As can be seen in Table 7, the sensitivity of the detection method is maintained down to concentrations of 50 ng total RNA. The specificity of the reaction was also maintained as can be seen by comparing the normalization ratios obtained in Tables 6 and 7.

Example 3 miRNA Profiling with Mixed Synthetic miRNAs

In this example, the ability of the detection reaction to detect various miRNAs present in mixed sample of synthetic miRNAs was examined. As with Example 1, the miRNAs were synthetically produced and the sequence of each miRNA is that shown in Table 1. The detection method used in the experiments described in Example 3 was identical to the method used in Example 1. As above, the columns in Table 8 represent the particular capture and detection oligonucleotides added to the reaction mixture specific for a given target RNA (indicated as Let-7a, Let-7b, Let-7c and Let-7g). The rows in Table 8 indicate which the target miRNA was added to the reaction mixture and the concentration at which each was added (each row represents a separate reaction). The sequences of each capture and detection oligonucleotide and the synthetic miRNAs are shown in Table 1.

Table 8 shows the assay specificity and sensitivity with mixed synthetic miRNAs. Row 1 is a negative control. Rows 2-4 are specific for Let-7a, Let-7b and Let-7c, respectively (each added at 10 fmol). Row 5 represents a mixture of 10 fmol of Let-7a together with 10 fmol of Let-7b. Row 6 represents a mixture of 10 fmol of Let-7a together with 5 fmol of Let-7b. Row 7 represents a mixture of 5 fmol of Let-7a together with 10 fmol of Let-7b. Similar combinations were tested for Let-7a and Let-7c (rows 8-10), and Let-7b and Let-7c (rows 11-13). As can be seen in Table 8, the signals detected correlated with the amount of miRNA target present in the reaction. While the results do indicate some cross hybridization (especially between highly homologous miRNAs such as Let-7b and Let-7c which differ in sequence by 1 nucleotide), this result indicates that the expression levels of various miRNAs can be monitored using the method disclosed.

Example 4

Generation of a ncRNA Signature for Breast Cancer

As discussed above, the methods of the present disclosure may be used to generate a ncRNA signature for a disease or condition. This example illustrates an example of a ncRNA signature generated for breast cancer where the ncRNA is a miRNA. In this example, patient RNA samples were purchased from Asterand (Detroit, Mich.). The patient RNA samples contained the target miRNAs. Tissue samples from a patient were laser micro-dissected and total RNA from the samples was extracted as described by the manufacturer. In two cases, pair matched samples were purchased, meaning that in addition to a cancer sample, a non-cancerous RNA sample from the breast (from the same subject) was also obtained. The non-cancerous RNA sample served as a baseline for miRNA expression. The pair matched samples used in the following example are designated 5386N (normal breast RNA sample from patient ID NO. 5386), 5386T (breast cancer RNA sample from patient ID NO. 5386), 31828N (normal breast RNA sample from patient ID NO. 31828), 31828T (breast cancer RNA sample from patient ID NO. 31828). In addition to the pair matched samples, addition RNA samples from breast tumor were also purchased and designated 5387T, 17260T, 4591T, 11793T, 12595T, 14292T, and 17054T. miRNA profiles were determined for each RNA sample.

In an initial screen, over 100 miRNA molecules were screened for each RNA sample obtained and a miRNA profile for each sample was created. The miRNAs analyzed included: let-7a, let-7b, let-7c, let-7d, let-7e, let-7f, let-7g, let-7i, miR-1, miR-100, miR-101, miR-101b, miR-103, miR-105, miR-106a, miR-106b, miR-107, miR-10a, miR-10b, miR-122a, miR-124a, miR-124a, miR-125a, miR-125b, miR-125b, miR-126, miR-127, miR-128a, miR-128b, miR-129, miR-130a, miR-130b, miR-131, miR-132, miR-133, miR-134, miR-135, miR-135b, miR-136, miR-137, miR-138, miR-139, miR-140, miR-141, miR-142-3p, miR-142-5p, miR-143, miR-144, miR-145, miR-146, miR-147, miR-148a, miR-148b, miR-149, miR-149, miR-150, miR-151, miR-152, miR-153, miR-153, miR-154, miR-155, miR-15a, miR-15b, miR-16, miR-17-3p, miR-17-5p, miR-178, miR-18, miR-181a, miR-181b, miR-181c, miR-182, miR-183, miR-184, miR-185, miR-186, miR-187, miR-188, miR-189, miR-190, miR-191, miR-192, miR-193, miR-194, miR-195, miR-196, miR-197, miR-198, miR-199a, miR-199b, miR-19b, miR-20, miR-200a, miR-200b, miR-200c, miR-201, miR-202, miR-203, miR-204, miR-205, miR-206, miR-207, miR-208, miR-21, miR-210, miR-211, miR-212, miR-213, miR-214, miR-215, miR-216, miR-217, miR-218, miR-219, miR-22, miR-220, miR-221, miR-222, miR-223, miR-224, miR-23a, miR-23b, miR-24, miR-25, miR-26a, miR-26b, miR-27a, miR-27b, miR-28, miR-290, miR-291-3p, miR-291-5p, miR-292-3p, miR-292-5p, miR-293, miR-294, miR-295, miR-296, miR-297, miR-298, miR-299, miR-29a, miR-29b, miR-29c, miR-300, miR-301, miR-30, miR-30a, miR-30b, miR-30c, miR-30d, miR-30e, miR-31, miR-32, miR-320, miR-321, miR-322, miR-323, miR-324-3p, miR-324-5p, miR-325, miR-326, miR-328, miR-329, miR-33, miR-330, miR-331, miR-337, miR-338, miR-339, miR-340, miR-341, miR-342, miR-344, miR-344, miR-345, miR-346, miR-34a, miR-34b, miR-34c, miR-350, miR-351, miR-7, miR-7b, miR-9, miR-92, miR-93, miR-95, miR-96, miR-98, miR-99a, miR-99b, miR-336, and miR-349. 5 sRNA was also examined.

Pairs of detection and capture oligonucleotides specific for the detection of each miRNA molecule were also synthesized. Each of the capture oligonucleotides was 10-12 nucleotides in length and contained an average of 3-4 LNA-modified nucleotides. The capture sequence was located on the 3' end of the target miRNA molecules. The capture oligonucleotides were synthesized and covalently coupled to color coded Luminex beads (per manufacturer's instructions). Each of the detection oligonucleotides were 8-10 nucleotides in length and contained and average of 2-3 LNA-modified nucleotides. Each detection oligonucleotide comprised a biotin tag on its 3' end. The detection sequence was located on the 5' end of the target miRNA molecule. The position and number of LNA-residues in each capture oligonucleotide and detection oligonucleotide were designed to give a $T_m$ of 45° C. for hybridization based on an online software tool provided by Exiqon.

The 114 pairs of capture and detection oligonucleotides were divided into 10 separate multiplex reactions. Each multiplex reaction contained 10 sets of capture and detection oligonucleotides specific for 10 distinct target miRNA molecules and 1 μg of total RNA from each of the above referenced patient RNA samples. For each target miRNA to be detected, about 3000 beads (containing ~0.5 pmol of capture oligonucleotide) and 0.5 pmol detection oligonucleotide were added in hybridization buffer (1×TMAC buffer, Sigma). The capture and detection oligonucleotides were added at the same time. The reaction was run at 45° C. for 1 hr. The target miRNA/capture oligonucleotide/detection oligonucleotide complexes were collected by centrifugation and excess liquid removed. Streptavidin-PE solution (Prozyme PJ/70S) was added per manufacturer's instructions and incubated for 10 min at 45° C. Samples were immediately read on the Luminex-100 detection platform (Luminex, Austin, Tex.).

Separate miRNA profiles were obtained from each of the RNA samples discussed above. The data from the miRNA profile analysis was analyzed. A subset of the target miRNA molecules was identified for further analysis. The nucleotide sequences for the miRNA molecules identified for further analysis and the nucleotide sequences of the capture and detection oligonucleotides for each of these miRNA molecules is shown in Table 1, along with the relevant SEQ ID NOS. The capital letters in the respective sequences indicates a LNA base. It should be noted that the nucleotide sequences indicated for the capture oligonucleotides can be modified by adding a spacer group as described in Example 1 above.

The raw data for these miRNA species is shown in Table 9 (with data expressed as mean fluorescent intensity, MFI). As can be seen in Table 9, several miRNA species showed differential expression between the normal breast tissue samples and the breast cancer samples. In addition, several miRNA species showed relatively constant expression between normal and breast cancer samples. These miRNA species can be used as internal references or internal controls to normalize the data if desired. Table 10 shows the data normalized to the mir-130a miRNA. To obtain the normalized reading, the MFI for each miRNA detected was divided by corresponding mir-130a MIF value. Although not required, the use of an internal reference allows differences between samples to be accounted for.

In Tables 9 and 10, the rows designate the miRNA target detected and the columns designate the patient RNA sample being analyzed. Neg represents a negative control where no sample RNA was added and Pos indicates a positive control (Table 9). As can be seen from Tables 9 and 10, the following target miRNA molecules showed altered expression between normal and cancer samples: mir-107, mir-15b, mir-103, mir-17-5p, mir-16, mir-126, mir-141, mir-142-3p, mir-143, mir-193, mir-199a, mir-29a, mir-195, mir-26a, mir-20, mir-128b, mir-217 and mir-219. As discussed above, the expression of mir-122a, mir299, mir-7b and mir130a remained essentially constant between normal and cancer samples.

Figure 2:
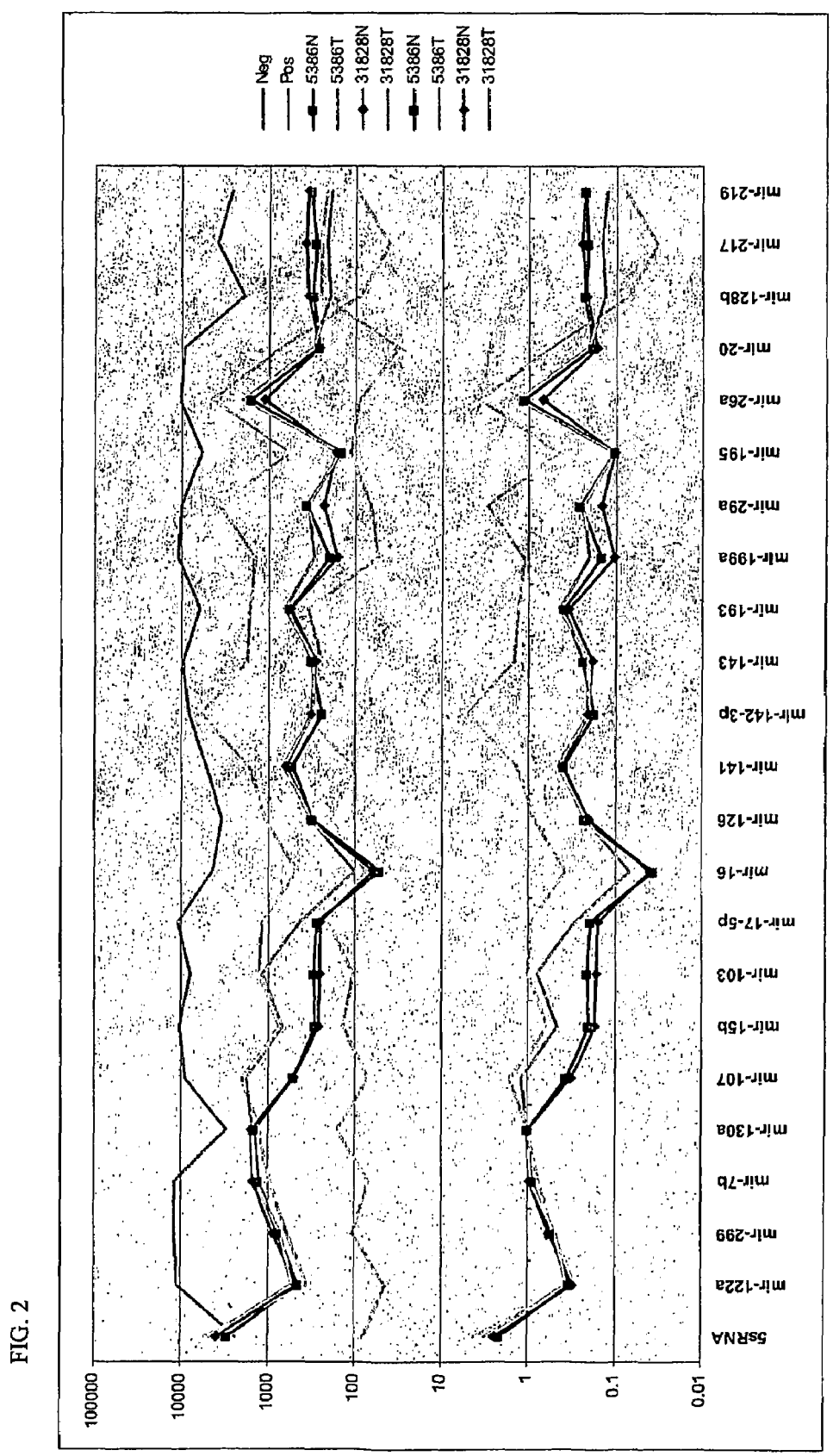
FIG. 2 shows the profiling of selected miRNA species from two pair matched samples (5386N and 5386T; 31828N and 31828T) of RNA obtained from normal breast tissue and breast cancer tissue derived from a single subject. On top half of the figure, the Y axis indicate the MFI of each miRNA detected; on the bottom half of the figure, the Y axis shows the normalized readings for each miRNA detected. The X axis shows the miRNA species detected.
Figure 3:
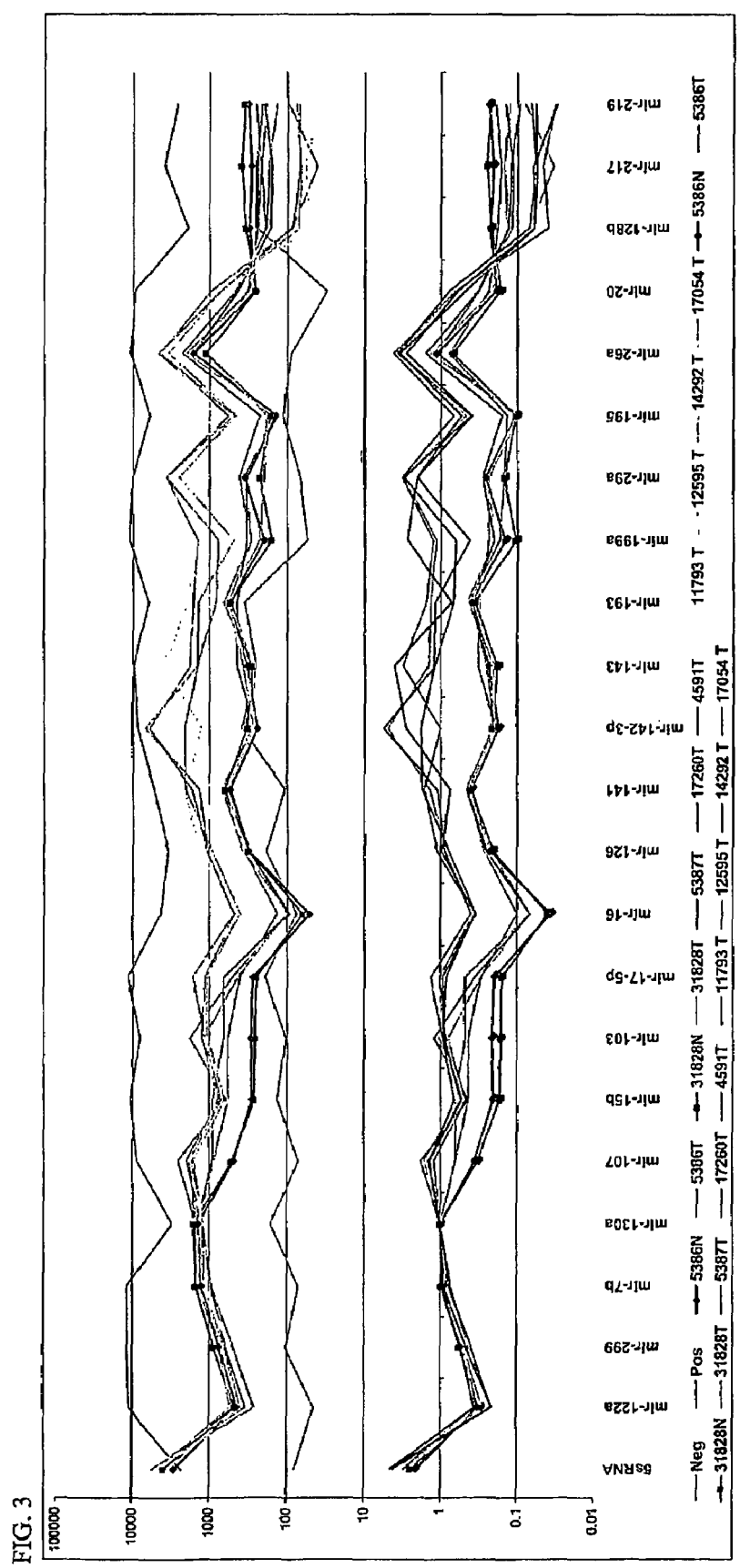
FIG. 3 shows the profiling of selected miRNA species from RNA obtained from normal breast tissue and breast cancer tissue. On top half of the figure, the Y axis indicate the MFI of each miRNA detected; on the bottom half of the figure, the Y axis shows the normalized MFI readings for each miRNA detected. The X axis shows the miRNA species detected.

Furthermore, the target miRNA molecules comprising the breast cancer miRNA signature can be further subdivided. For Example, as shown in FIGS. 2 and 3, mir-107, mir-15b and mir-103 showed altered (in this case increased) expression in all the breast cancer samples as compared to normal samples. However, mir-17-5p, mir-16, mir-126, mir-141, mir-142-3p, mir-143, mir-193, mir-199a, mir-29a, mir-195, mir-26a, mir-20, mir-128b, mir-217 and mir-219 showed mixed results depending on the breast cancer sample analyzed. mir-17-5p, mir-16, mir-126, mir-141, mir-142-3p, mir-143, mir-193, mir-199a, mir-29a, mir-195, mir-26a, mir-20, mir-128b, mir-217 and mir-219 showed altered expression as compared to normal samples in the 5386T, 12595T, 14292T, 11793T and 17054T breast cancer samples. For example, mir-142-3p showed increased expression in the above breast cancer samples, while mir-219 showed decreased expression in the above breast cancer samples. In contrast, mir-17-5p, mir-16, mir-126, mir-141, mir-142-3p, mir-143, mir-193, mir-199a, mir-29a, mir-195, mir-26a, mir-20, mir-128b, mir-217 and mir-219 essentially mirrored the miRNA profile of the normal breast tissue samples in the 5387T, 17260T, and 4591T breast cancer samples.

This data suggests that a breast cancer miRNA signature comprises at least mir-107, mir-15b and mir-103. Other miRNA species may be included in the breast cancer miRNA signature as indicated in Tables 9 and 10 and FIGS. 2 and 3. The differences observed in the remaining miRNA species may be due to differences in the state of progression of the breast cancer from which the sample was taken or due to other molecular differences. The differences in expression patterns may be a useful diagnostic tool for sub-classification of breast cancer patients, since the miRNA profiles fell into two distinct groups. The miRNA profiles for samples 11793T, 12595T, 14292T, and 17054T are similar to that of the 5386T, while the miRNA profiles for samples 5387T, 17260T, and 4591T are similar to that of the 31828T.

The present example demonstrates that using the ncRNA detection methods disclosed, ncRNA profiles (in this case miRNA) can be generated and that the ncRNA profiles may be used to create a ncRNA signature for a particular disease or condition (in this case, breast cancer). In addition, the ncRNA signature can sub-classify breast cancer samples based on the expression profile of the ncRNA species (in this case miRNA) as shown in FIG. 3. A patient ncRNA profile may be obtained as described and compared to the ncRNA signature for the disease in order to diagnose said patient with a disease or condition, or at risk for said disease or condition. Each ncRNA in the ncRNA signature is examined against the patient ncRNA profile to make the diagnosis. The diagnosis may be made by comparing the ncRNA levels in the patient profile against the ncRNA levels in the ncRNA signature. Therefore, it can be determined if each ncRNA value suggests a diagnosis or whether one or more of such ncRNA value suggests a diagnosis. This determination can be made by a visual analysis of the data, applying a cut-off/threshold value for each ncRNA or through the use of statistical models (such as but not limited to the model described in Example 6 below).

Example 5

Generation of a ncRNA Signature for Glioma

This example illustrates an example of a ncRNA signature generated for glioma where the ncRNA is a miRNA. In this example, RNA samples were obtained from a series of glioma cell lines and a normal neuronal cell line. RNA extracted was accomplished using standard methodology. The glioma cell lines used were LN-215, LN-340, U343MG, U373MG, LN401, LN405, LN464 and U87MG. These cell lines are described in Ishii et al (Brain Pathol. 9:469-479, 1999). In addition, a normal neuronal cell line, designated HA, served as a baseline for miRNA expression. The miRNA detection methods described in Example 4 were used in this example.

miRNA profiles were obtained from RNA samples from each of the cell lines discussed above. The data from the miRNA profile analysis was analyzed. A subset of the 114 target miRNA molecules was identified for further analysis. The raw data for these miRNA species is shown in Table 11 (with data expressed as mean fluorescent intensity, MFI). As can be seen in Table 11, several miRNA species showed differential expression between the normal neuronal cell line and the glioma cell lines. In addition, several miRNA species showed relatively constant expression between the normal neuronal cell line and the glioma cell lines. These miRNA species can be used as internal references or internal controls to normalize the data if desired. Table 12 shows the data normalized to the mir-130a miRNA. To obtain the normalized reading, the MFI for each miRNA detected was divided by corresponding mir-130a MFI value. Although not required, the use of an internal reference allows differences between samples to be accounted for.

In Tables 11 and 12, the rows designate the miRNA target detected and the columns designate the RNA sample being analyzed. Neg represents a negative control where no sample RNA was added and Pos indicates a positive control (Table 11). As can be seen from Tables 11 and 12, the following target miRNA molecules showed altered expression between the normal neuronal cell line and the glioma cell lines: mir-141, mir-143, mir-23b, mir-15b, mir-293, mir-17-p3 and mir-320. The expression of mir-17-5p, mir214 and mir130a remained essentially constant between the normal neuronal cell line and the glioma cell lines.

Figure 4:
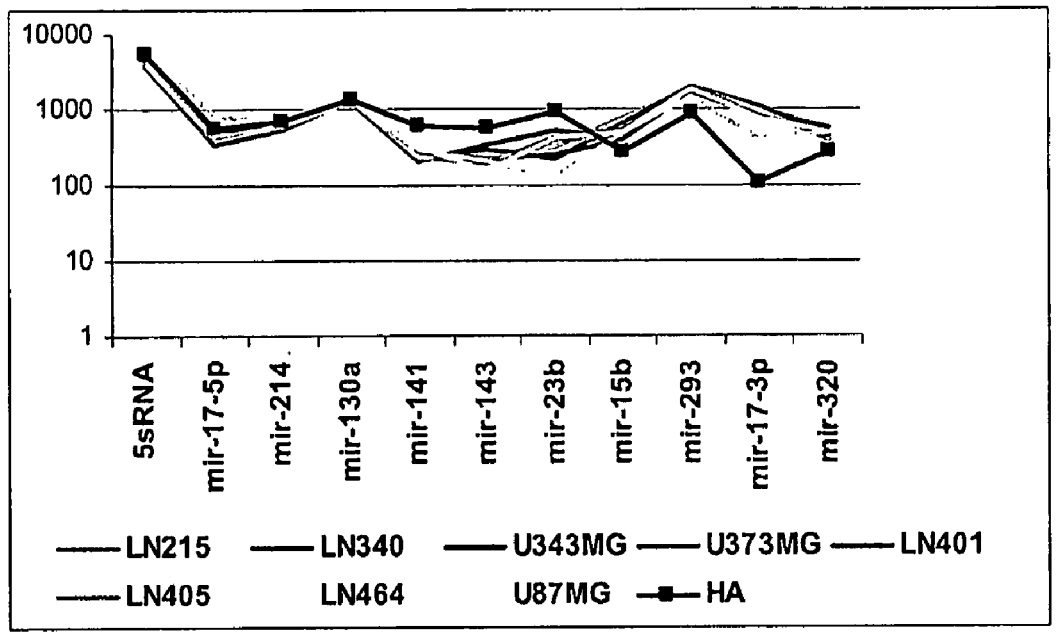
FIG. 4 shows the profiling of selected miRNA species from RNA obtained from normal neuronal cells and selected glioma cell lines. The Y axis indicates the MFI of each miRNA detected and the X axis indicates the miRNA species detected.
Figure 5:
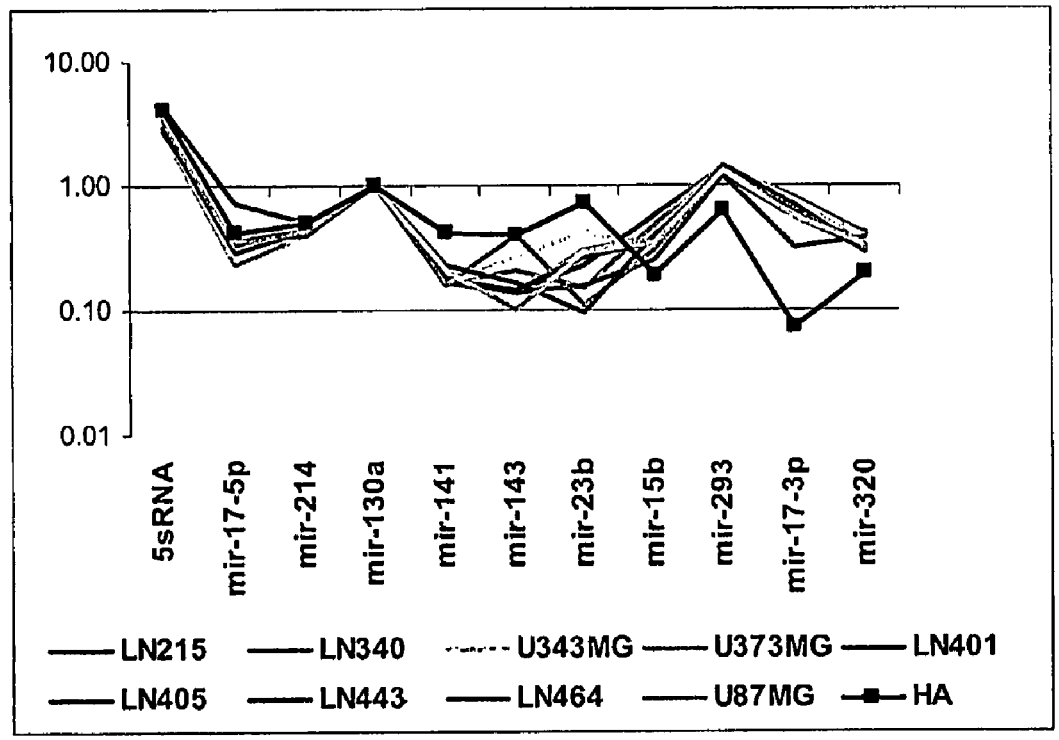
FIG. 5 shows the profiling of selected miRNA species from RNA obtained from normal neuronal cells and selected glioma cell lines. The Y axis shows the normalized MFI readings for each miRNA detected and the X axis indicates the miRNA species detected.

FIGS. 4 and 5 show the graphical representations of the miRNA profiles for the cell lines examined in this example. FIG. 4 shows the data plotted as a function of MFI (y axis), while FIG. 5 shows the same data plotted using MFI values normalized to the MFI value of mir-130a (y axis). The x axis of both figures represents the miRNA species being detected. As can be seen, mir-141, mir-143, mir-23b, mir-15b, mir-293, mir-17-p3 and mir-320 showed altered (both increased and decreased) expression in essentially all of the glioma cell lines as compared to normal neuronal sample.

This data suggests that a glioma miRNA signature comprises at least mir-141, mir-23b, mir-293, mir-17-3p and mir-320. Other miRNA species may be included in the breast cancer miRNA signature as indicated in Tables 11 and 12 and FIGS. 4 and 5. The differences observed in the remaining miRNA species (such as mir-143 and mir-15b) may be due to differences in the state of progression of the breast cancer from which the sample was taken or due to other molecular differences.

The present example demonstrates that using the ncRNA detection methods disclosed, ncRNA profiles (in this case miRNA) can be generated and that the ncRNA profiles may be used to create a ncRNA signature for a particular disease or condition (in this case, glioma).

Example 6

Statistical Methods for ncRNA Signatures

In order to utilize the power of the ncRNA signatures described herein, a statistical approach may be applied to the data generated. A number of statistical approaches may be used. In one embodiment, a likelihood ratio is used to describe the ncRNA signature for a given disease or condition and/or to classify a subject as having/susceptible to or not having/not susceptible to the disease or condition. In this approach, the assumption is made that the population distribution of the miRNA level is approximate to a Gaussian distribution function. In calculating likelihood ratios, the Gaussian 'height' is used instead of the probability:

$$f(X) = 1/(\sigma\sqrt{2\pi}) \cdot e^{-1/2 \cdot ((X-\mu)/\sigma)^2} \qquad 1$$

In equation 1, $f(x)$ is the Gaussian height for the applied parameter x (x may be a normal or abnormal population); $\mu$ is the population mean for parameter x and $\partial$ is the population standard deviation. Equation 1 can be examined in three parts. On the left hand side of the equation the expression $1/(\partial\sqrt{2\pi})$ controls the maximum height of the Gaussian peak. The central portion involving 'e' converts the output of the third section of the equation into the correctly shaped envelope. The final section calculates a standard deviation defining how far from the centre of the population distribution, the value x lies. This value is also known as the "Mahalanobis distance".

The Gaussian heights for each signature miRNAs are determined for 'normal' and 'abnormal' parameters (see graph below). Note that $\mu1$ and $\mu2$ are the population specific mean. The $\mu1$ value is used to calculate the Gaussian height of a miRNA level for the normal population, and the $\mu2$ value is used to calculate the Gaussian height of a miRNA level in the abnormal population.

Figure 6:
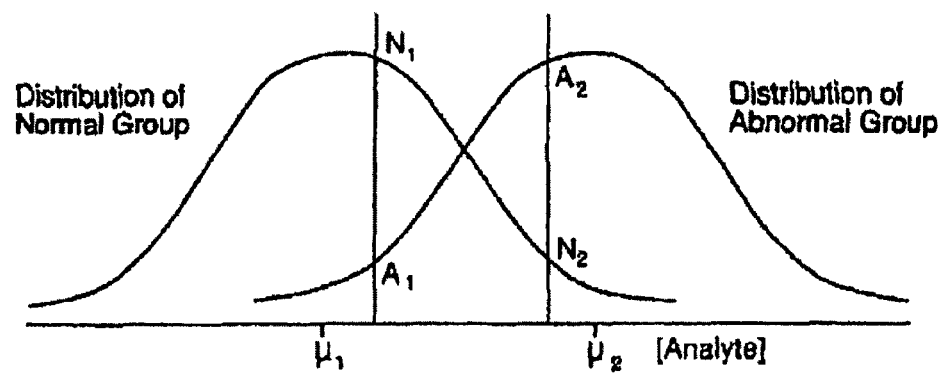
FIG. 6 shows two scenarios: In case 1, the ratio of the height on the 'normal' curve and the height on the 'abnormal' curve ($N_1/A_1$) is approximately 4; for case two ($N_2/A_2$) the ratio is approximately 0.25. In another words, if the miRNA level measured from a patient is close to the "normal" mean, it is most likely that the patient is normal (not characterized as having a given disease or condition); if, however, the miRNA level is close to the mean of the "abnormal" population, then, the subject is most likely abnormal (characterized as having or sat risk for the disease or condition).

FIG. 6 shows two scenarios: In case 1, the ratio of the height on the 'normal' curve and the height on the 'abnormal' curve ($N_1/A_1$) is approximately 4; for case two ($N_2/A_2$) the ratio is approximately 0.25. In another words, if the miRNA level measured from a patient is close to the "normal" mean, it is most likely that the patient is normal (not characterized as having a given disease or condition); if, however, the miRNA level is close to the mean of the "abnormal" population, then, the subject is most likely abnormal (characterized as having or sat risk for the disease or condition). Therefore, the likelihood ratio indicates the probability that a given subject is suffering from or at risk for a given disease or condition based on the levels of certain ncRNA molecules identified in the subjects profile.

One advantage of using Gaussian heights is the capability of combining the predictive power of multiple, independent miRNAs levels obtained in the profile of a subject. The combined likelihood, or probability, that a subject is suffering from or at risk for a disease or condition can be calculated using equation (2). In Equation (2), LRt represents the summed Gaussian height for the abnormal population and LRn represents the summed Gaussian height for the normal population $$\text{Probability} = (LRt)/(LRt+LRn) \qquad 2$$

where LRt=LR1$t$\*LR2$t$\*LR3$t$ . . . LRnt, and LRn=LR1$n$\*LR2$n$\*LR3$n$ . . . LRnn.

In order to demonstrate the application of this statistical approach, the normalized data obtained for mir-130a, mir-107, mir-15b and mir-103 as described in Example 4 (Table 10) is used. From the normalized data, the means and standard deviation values for the cancer and normal samples (the populations) are determined. In this example, the standard deviation for the normal samples was set to 0.2000. The Gaussian height values for mir-107, mir-15b, and mir-103 are calculated for each of the samples. First, the mean and standard deviation values for the normal samples are used to obtain the "normal" Gaussian heights; then, the mean and standard deviation values for the breast cancer samples to obtain the "abnormal" Gaussian heights. The likelihood ratio is generated as the ratio between the GH-Abnormal and GH-Normal. Once the individual likelihood ratios are established, a combined risk factor or probability factor (indicative of whether an individual is suffering from or at risk for a disease/condition) is determined by multiplying the individual likelihood ratios determined for each miRNA species in a subjects profile. The calculations described above are shown in Table 13.

Example 7

Determination of Potential Therapeutic Targets Identified by ncRNA Profiling

As described above, the detection methods disclosed may be used to identify potential drug targets for the treatment of a disease or condition. ncRNA signatures for a particular disease or condition may be created. By determining the identity of the ncRNA species that characterize a particular disease or condition, the identity of molecular targets involved in the molecular pathways responsible for the disease state or condition may be identified. For example, miRNA molecules have been known to regulate gene expression by either degrading mRNA for a protein and/or interfering with the transcription of a protein. These molecular targets may provide novel therapeutic candidates for drug development for the treatment and/or prevention of the disease or condition. In such a method, the ncRNA signature for a disease or condition is obtained as described above. The ncRNA molecules that characterize the disease or condition are noted. The identity of the ncRNA molecules is used to determine the molecular targets involved in the molecular pathways of the disease or condition. In a specific embodiment, the ncRNA is a miRNA.

A computer program may be used to compare the sequence of one or more ncRNA molecules in the ncRNA signature to commercially available or proprietary databases containing genomics information to identify targets to which a ncRNA molecule may bind. Such a target is a potential therapeutic candidate for drug development. Any program/software capable of performing the comparison may be used. In this example, a publicly available algorithm was used to carry out the comparison (Enright et al. PLoS Biol 2(11): e363)

In order to demonstrate the application of this method, the normalized data obtained for mir-107, mir-15b and mir-103 as described in Example 4 (Tables 9 and 10 and FIGS. 2 and 3) is used. Example 4 identified mir-107, mir-15b and mir-103 as comprising a miRNA signature for breast cancer. The sequences of these miRNA molecules were queried against a genomic database containing nucleic acid sequence information to identify targets containing sequences to which the identified miRNA molecule might bind. A number of potential targets were identified as listed in Table 14. It should be noted that Table 14 is a partial list of candidate therapeutic targets.

As can be seen from Table 14, certain proteins are identified as candidate therapeutic targets for each of mir-107, mir-15b and mir-103 (such as TAR DNA-binding protein 43), while other proteins are identified as candidate therapeutic targets for a subset of these miRNA molecules (for example, MAP-1A is identified by mir-103 and mir-107, but not by mir-15b). The identification of target by utilization of this approach can yield insight into targets involved in the molecular mechanism of the disease or condition and can provide novel candidates for drug development.

What is claimed is:

1. A method for creating a signature ncRNA profile for a disease state or condition, said method comprising:
   a. determining a first ncRNA profile from a first source, said first source being characterized as being free from said disease state or condition;
   b. determining a second ncRNA profile from a second source, said second source characterized as being positive for said disease state or condition, said first and second ncRNA profile being obtained according to a method for determining a profile of a plurality of target ncRNA molecules in a RNA sample, said method comprising the steps of:
      i. providing said RNA sample from a subject, said sample containing said plurality of target ncRNAs;
      ii. contacting said sample with a first oligonucleotide specific for each of said target ncRNAs to be detected under conditions appropriate to faun a complex between said first oligonucleotides and said target ncRNAs, each of said first oligonucleotides comprising a first signal generator to generate a first detectable signal and each of said first oligonucleotides having a first Tm for binding each of said target ncRNAs that is substantially the same;
      iii. contacting said sample with a second oligonucleotide capable of binding each of said target ncRNAs to be detected under conditions appropriate to form a complex between said second oligonucleotides and said target ncRNAs, said second oligonucleotide comprising a second signal generator to generate a second detectable signal and each of said second oligonucleotides having a second Tm for binding each of said target ncRNAs that is substantially the same;
      iv. determining the presence of said plurality of target ncRNA in said sample by measuring the first and second detectable signals; and
      v. generating a profile of the sample based on the target ncRNAs detected
   c. comparing said first and second ncRNA profiles and identifying those ncRNA molecules that are altered in said second ncRNA profile to create a signature ncRNA profile for said disease state or condition;
   where said disease state is breast cancer and said signature ncRNA profile comprises mir-107, mir-15B and mir-103.

2. The method of claim 1 where said signature ncRNA further comprises at least one of: mir-17-5p, mir-16, mir-126, mir-141, mir-193, mir29a, mir-195, mir-26a, mir20, mir128b, mir217 and mir219.

3. A method for creating a signature ncRNA profile for a disease state or condition, said method comprising:
   a. determining a first ncRNA profile from a first source, said first source being characterized as being free from said disease state or condition;
   b. determining a second ncRNA profile from a second source, said second source characterized as being positive for said disease state or condition, said first and second ncRNA profile being obtained according to a method for determining a profile of a plurality of target ncRNA molecules in a RNA sample, said method comprising the steps of:
      i. providing said RNA sample from a subject, said sample containing said plurality of target ncRNAs;
      ii. contacting said sample with a first oligonucleotide specific for each of said target ncRNAs to be detected under conditions appropriate to form a complex between said first oligonucleotides and said target ncRNAs, each of said first oligonucleotides comprising a first signal generator to generate a first detectable signal and each of said first oligonucleotides having a first Tm for binding each of said target ncRNAs that is substantially the same;
      iii. contacting said sample with a second oligonucleotide capable of binding each of said target ncRNAs to be detected under conditions appropriate to form a complex between said second oligonucleotides and said target ncRNAs, said second oligonucleotide comprising a second signal generator to generate a second detectable signal and each of said second oligonucleotides having a second Tm for binding each of said target ncRNAs that is substantially the same;
      iv. determining the presence of said plurality of target ncRNA in said sample by measuring the first and second detectable signals; and
      v. generating a profile of the sample based on the target ncRNAs detected
   c. comparing said first and second ncRNA profiles and identifying those ncRNA molecules that are altered in said second ncRNA profile to create a signature ncRNA profile for said disease state or condition;
   where said disease state is glioma and said signature miRNA profile comprises mir-141, mir-23b and mir-17-3p.

4. The method of claim 3 where said signature ncRNA further comprises at least one of: mir-143, mir-15b, mir-293 and mir-320.

5. The method of claim 1 where said profile is used to diagnose a subject in need of said diagnosis.

6. The method of claim 1 where said profile is used to identify candidate therapeutic targets for drug development.

7. A method for the simultaneous detection of a plurality of distinct target ncRNAs, said method comprising the steps of:
   a. providing a RNA sample from a subject, said sample containing said plurality of target ncRNAs;
   b. contacting said sample with a capture oligonucleotide specific for each of the target ncRNAs to be detected, each of said capture oligonucleotides coupled to a microsphere having a distinct first detectable signal for each target ncRNA to be detected, wherein a portion the capture oligonucleotide is complementary to a portion of each target ncRNA to be detected;
   c. contacting said sample with a detection oligonucleotide specific for each of the target ncRNAs to be detected, each of said detection oligonucleotides coupled to a biotin tag, wherein a portion of the detection oligonucleotide is complementary to a portion of each target ncRNA to be detected;
d. contacting said sample with streptavidin coupled to a signal generator to generate a second detectable signal, the second detectable signal being distinct from the first detectable signal;
e. determining the presence of the plurality of target ncRNAs by measuring the simultaneous presence of the first and second detectable signals.

8. The method of claim 7 where said ncRNA is a miRNA.

9. The method of claim 7 where said first detectable signal is different for each of said capture oligonucleotides that binds a distinct ncRNA in said plurality of target ncRNAs.

10. The method of claim 7 where said capture oligonucleotide and said detection oligonucleotide are added simultaneously.

11. The method of claim 7 where said capture and detection oligonucleotides are added sequentially.

12. The method of claim 7 wherein each capture oligonucleotide has a first Tm for binding each said ncRNA, each detection oligonucleotide has a second Tm for binding each said ncRNA, and each of said first Tms and each of said second Tms are substantially the same.

13. The method of claim 7 where at least one of said capture oligonucleotide and said detection oligonucleotide comprises at least one modified nucleotide.

14. The method of claim 13 where said modified nucleotide is a locked nucleic acid.

15. The method of claim 7 where said first and second detectable signals comprises an optical signature.

16. The method of claim 7 where said first and second detectable signals are a fluorescent signal.

17. The method of claim 7 where said capture oligonucleotide is 8-12 nucleotides in length and said detection oligonucleotide is 8-12 nucleotides in length.

18. The method of claim 7 where said method is used to generate a profile of said target ncRNAs present in said sample.

19. The method of claim 7 where said sample is derived from a human subject.

20. The method of claim 7 where said RNA sample is not size fractionated to increase the proportion of a lower molecular weight RNA species.

21. The method of claim 7 further comprising generating a profile of the sample based on the target ncRNAs detected.

22. A method of creating a signature ncRNA profile for a disease or condition, said method comprising the steps of:
a. obtaining a ncRNA profile from a sample characterized as having said disease or condition to create a first profile, said profile being obtained by the method of claim 21;
b. obtaining a ncRNA profile from a sample characterized as normal to create a second profile said profile being obtained by the methods of claim 21; and
c. identifying one or more ncRNA molecules in said first profile that distinguish said first profile from said second profile
d. generating a signature ncRNA profile for the disease based on the ncRNA molecules in the first profile that distinguish it from the second profile.

23. The method of claim 22 where said ncRNA is a miRNA.

24. The method of claim 22 where said disease is glioma or breast cancer.

25. The method of claim 22 where said subject is a human.

26. A method of diagnosing a subject with a disease or condition, said method comprising the steps of:
a. determining a subject ncRNA profile from said subject according to claim 21;
b. comparing said subject ncRNA profile to a ncRNA profile for said disease or condition, said subject ncRNA profile and said ncRNA profile for said disease or condition being determined according to the method of claim 21;
c. diagnosing said subject with said disease or condition based on a comparison of said subject ncRNA profile to said ncRNA profile for said disease or condition.

27. The method of claim 26 where said ncRNA is a miRNA.

28. The method of claim 26 where said disease is glioma or breast cancer.

29. The method of claim 26 where said subject is a human.

30. A method of screening to identify a gene involved in a disease or condition, said method comprising the steps of:
a. obtaining a signature ncRNA profile for said disease or condition, said signature ncRNA profile being obtained by the method of claim 22; and
b. determining a molecular target with which one said ncRNAs identified in signature ncRNA profile interact; and
c. identifying the gene associated with the molecular target.

31. The method of claim 30 where said ncRNA is a miRNA.

32. The method of claim 30 where said disease is glioma or breast cancer.

33. The method of claim 30 where said subject is a human.

34. The method of claim 30 where said determining step is accomplished with the aid of an algorithm.

* * * * *

SEQUENCE LISTING

<160> NUMBER OF SEQ ID NOS: 98

<210> SEQ ID NO 1
<211> LENGTH: 23
<212> TYPE: RNA
<213> ORGANISM: Homo sapiens

<400> SEQUENCE: 1
uggaguguga caauggguguu ugu                                              23

<210> SEQ ID NO 2
<211> LENGTH: 12
<212> TYPE: DNA
<213> ORGANISM: Artificial
<220> FEATURE:
<223> OTHER INFORMATION: oligonucleotide

<400> SEQUENCE: 2
acaaacacca tt                                                           12

<210> SEQ ID NO 3
<211> LENGTH: 11
<212> TYPE: DNA
<213> ORGANISM: Artificial
<220> FEATURE:
<223> OTHER INFORMATION: oligonucleotide

<400> SEQUENCE: 3
gtcacactcc a                                                            11

<210> SEQ ID NO 4
<211> LENGTH: 22
<212> TYPE: RNA
<213> ORGANISM: Homo sapiens

<400> SEQUENCE: 4
ugguuuaccg ucccacauac au                                                22

<210> SEQ ID NO 5
<211> LENGTH: 11
<212> TYPE: DNA
<213> ORGANISM: Artificial
<220> FEATURE:
<223> OTHER INFORMATION: oligonucleotide

<400> SEQUENCE: 5
atgtatgtgg g                                                            11

<210> SEQ ID NO 6
<211> LENGTH: 11
<212> TYPE: DNA
<213> ORGANISM: Artificial
<220> FEATURE:
<223> OTHER INFORMATION: oligonucleotide

<400> SEQUENCE: 6
acggtaaacc a                                                            11

<210> SEQ ID NO 7
<211> LENGTH: 21
<212> TYPE: RNA
<213> ORGANISM: Homo sapiens

```
<400> SEQUENCE: 7
uggaagacuu gugauuuugu u                                      21

<210> SEQ ID NO 8
<211> LENGTH: 11
<212> TYPE: DNA
<213> ORGANISM: Artificial
<220> FEATURE:
<223> OTHER INFORMATION: oligonucleotide

<400> SEQUENCE: 8
acaaaatcac a                                                 11

<210> SEQ ID NO 9
<211> LENGTH: 9
<212> TYPE: DNA
<213> ORGANISM: Artificial
<220> FEATURE:
<223> OTHER INFORMATION: oligonucleotide

<400> SEQUENCE: 9 agtcttcca                                                     9

<210> SEQ ID NO 10
<211> LENGTH: 22
<212> TYPE: RNA
<213> ORGANISM: Homo sapiens

<400> SEQUENCE: 10
cagugcaaug uuaaaagggc au                                     22

<210> SEQ ID NO 11
<211> LENGTH: 12
<212> TYPE: DNA
<213> ORGANISM: Artificial
<220> FEATURE:
<223> OTHER INFORMATION: oligonucleotide

<400> SEQUENCE: 11
atgccctttt aa                                                12

<210> SEQ ID NO 12
<211> LENGTH: 10
<212> TYPE: DNA
<213> ORGANISM: Artificial
<220> FEATURE:
<223> OTHER INFORMATION: oligonucleotide

<400> SEQUENCE: 12
cattgcactg                                                   10

<210> SEQ ID NO 13
<211> LENGTH: 23
<212> TYPE: RNA
<213> ORGANISM: Homo sapiens

<400> SEQUENCE: 13
agcagcauug uacagggcua uca                                    23

<210> SEQ ID NO 14
<211> LENGTH: 12
<212> TYPE: DNA
<213> ORGANISM: Artificial
<220> FEATURE:
<223> OTHER INFORMATION: oligonucleotide
```

```
<400> SEQUENCE: 14
tgatagccct gt                                                    12

<210> SEQ ID NO 15
<211> LENGTH: 11
<212> TYPE: DNA
<213> ORGANISM: Artificial
<220> FEATURE:
<223> OTHER INFORMATION: oligonucleotide

<400> SEQUENCE: 15
acaatgctgc t                                                     11

<210> SEQ ID NO 16
<211> LENGTH: 22
<212> TYPE: RNA
<213> ORGANISM: Homo sapiens

<400> SEQUENCE: 16
uagcagcaca ucaugguuua ca                                         22

<210> SEQ ID NO 17
<211> LENGTH: 12
<212> TYPE: DNA
<213> ORGANISM: Artificial
<220> FEATURE:
<223> OTHER INFORMATION: oligonucleotide

<400> SEQUENCE: 17
tgtaaaccat ga                                                    12

<210> SEQ ID NO 18
<211> LENGTH: 10
<212> TYPE: DNA
<213> ORGANISM: Artificial
<220> FEATURE:
<223> OTHER INFORMATION: oligonucleotide

<400> SEQUENCE: 18
tgtgctgcta                                                       10

<210> SEQ ID NO 19
<211> LENGTH: 23
<212> TYPE: RNA
<213> ORGANISM: Homo sapiens

<400> SEQUENCE: 19
agcagcauug uacagggcua uga                                        23

<210> SEQ ID NO 20
<211> LENGTH: 12
<212> TYPE: DNA
<213> ORGANISM: Artificial
<220> FEATURE:
<223> OTHER INFORMATION: oligonucleotide

<400> SEQUENCE: 20
tcatagccct gt                                                    12

<210> SEQ ID NO 21
<211> LENGTH: 11
<212> TYPE: DNA
<213> ORGANISM: Artificial
<220> FEATURE:
<223> OTHER INFORMATION: oligonucleotide
```

-continued

```
<400> SEQUENCE: 21
acaatgctgc t                                                          11

<210> SEQ ID NO 22
<211> LENGTH: 24
<212> TYPE: RNA
<213> ORGANISM: Homo sapiens

<400> SEQUENCE: 22
caaagugcuu acagugcagg uagu                                            24

<210> SEQ ID NO 23
<211> LENGTH: 12
<212> TYPE: DNA
<213> ORGANISM: Artificial
<220> FEATURE:
<223> OTHER INFORMATION: oligonucleotide

<400> SEQUENCE: 23
actacctgca ct                                                         12

<210> SEQ ID NO 24
<211> LENGTH: 12
<212> TYPE: DNA
<213> ORGANISM: Artificial
<220> FEATURE:
<223> OTHER INFORMATION: oligonucleotide

<400> SEQUENCE: 24
gtaagcactt tg                                                         12

<210> SEQ ID NO 25
<211> LENGTH: 22
<212> TYPE: RNA
<213> ORGANISM: Homo sapiens

<400> SEQUENCE: 25
uagcagcacg uaaauauugg cg                                              22

<210> SEQ ID NO 26
<211> LENGTH: 12
<212> TYPE: DNA
<213> ORGANISM: Artificial
<220> FEATURE:
<223> OTHER INFORMATION: oligonucleotide

<400> SEQUENCE: 26
cgccaatatt ta                                                         12

<210> SEQ ID NO 27
<211> LENGTH: 10
<212> TYPE: DNA
<213> ORGANISM: Artificial
<220> FEATURE:
<223> OTHER INFORMATION: oligonucleotide

<400> SEQUENCE: 27
cgtgctgcta                                                            10

<210> SEQ ID NO 28
<211> LENGTH: 21
<212> TYPE: RNA
<213> ORGANISM: Homo sapiens
```

```
<400> SEQUENCE: 28
ucguaccgug aguaauaaug c                                              21

<210> SEQ ID NO 29
<211> LENGTH: 11
<212> TYPE: DNA
<213> ORGANISM: Artificial
<220> FEATURE:
<223> OTHER INFORMATION: oligonucleotide

<400> SEQUENCE: 29
gcattattac t                                                         11

<210> SEQ ID NO 30
<211> LENGTH: 10
<212> TYPE: DNA
<213> ORGANISM: Artificial
<220> FEATURE:
<223> OTHER INFORMATION: oligonucleotide

<400> SEQUENCE: 30
cacggtacga                                                           10

<210> SEQ ID NO 31
<211> LENGTH: 21
<212> TYPE: RNA
<213> ORGANISM: Homo sapiens

<400> SEQUENCE: 31
aacacugucu gguaaagaug g                                              21

<210> SEQ ID NO 32
<211> LENGTH: 11
<212> TYPE: DNA
<213> ORGANISM: Artificial
<220> FEATURE:
<223> OTHER INFORMATION: oligonucleotide

<400> SEQUENCE: 32
ccatctttac c                                                         11

<210> SEQ ID NO 33
<211> LENGTH: 10
<212> TYPE: DNA
<213> ORGANISM: Artificial
<220> FEATURE:
<223> OTHER INFORMATION: oligonucleotide

<400> SEQUENCE: 33
agacagtgtt                                                           10

<210> SEQ ID NO 34
<211> LENGTH: 22
<212> TYPE: RNA
<213> ORGANISM: Homo sapiens

<400> SEQUENCE: 34
uguaguguuu ccuacuuuau gg                                             22

<210> SEQ ID NO 35
<211> LENGTH: 12
<212> TYPE: DNA
<213> ORGANISM: Artificial
<220> FEATURE:
<223> OTHER INFORMATION: oligonucleotide
```

```
<400> SEQUENCE: 35
ccataaagta gg                                                            12

<210> SEQ ID NO 36
<211> LENGTH: 10
<212> TYPE: DNA
<213> ORGANISM: Artificial
<220> FEATURE:
<223> OTHER INFORMATION: oligonucleotide

<400> SEQUENCE: 36
aaacactaca                                                               10

<210> SEQ ID NO 37
<211> LENGTH: 22
<212> TYPE: RNA
<213> ORGANISM: Homo sapiens

<400> SEQUENCE: 37
ugagaugaag cacuguagcu ca                                                 22

<210> SEQ ID NO 38
<211> LENGTH: 12
<212> TYPE: DNA
<213> ORGANISM: Artificial
<220> FEATURE:
<223> OTHER INFORMATION: oligonucleotide

<400> SEQUENCE: 38
tgagctacag tg                                                            12

<210> SEQ ID NO 39
<211> LENGTH: 10
<212> TYPE: DNA
<213> ORGANISM: Artificial
<220> FEATURE:
<223> OTHER INFORMATION: oligonucleotide

<400> SEQUENCE: 39
cttcatctca                                                               10

<210> SEQ ID NO 40
<211> LENGTH: 21
<212> TYPE: RNA
<213> ORGANISM: Homo sapiens

<400> SEQUENCE: 40
aacuggccua caaagcccca g                                                  21

<210> SEQ ID NO 41
<211> LENGTH: 11
<212> TYPE: DNA
<213> ORGANISM: Artificial
<220> FEATURE:
<223> OTHER INFORMATION: oligonucleotide

<400> SEQUENCE: 41
ctgggacttt g                                                             11

<210> SEQ ID NO 42
<211> LENGTH: 10
<212> TYPE: DNA
<213> ORGANISM: Artificial
<220> FEATURE:
<223> OTHER INFORMATION: oligonucleotide
```

```
<400> SEQUENCE: 42
taggccagtt                                                              10

<210> SEQ ID NO 43
<211> LENGTH: 23
<212> TYPE: RNA
<213> ORGANISM: Homo sapiens

<400> SEQUENCE: 43
cccaguguuc agacuaccug uuc                                               23

<210> SEQ ID NO 44
<211> LENGTH: 12
<212> TYPE: DNA
<213> ORGANISM: Artificial
<220> FEATURE:
<223> OTHER INFORMATION: oligonucleotide

<400> SEQUENCE: 44
acaggtagtc tg                                                           12

<210> SEQ ID NO 45
<211> LENGTH: 9
<212> TYPE: DNA
<213> ORGANISM: Artificial
<220> FEATURE:
<223> OTHER INFORMATION: oligonucleotide

<400> SEQUENCE: 45 aacactggg                                                                9

<210> SEQ ID NO 46
<211> LENGTH: 22
<212> TYPE: RNA
<213> ORGANISM: Homo sapiens

<400> SEQUENCE: 46
cuagcaccau cugaaaucgg uu                                                22

<210> SEQ ID NO 47
<211> LENGTH: 12
<212> TYPE: DNA
<213> ORGANISM: Artificial
<220> FEATURE:
<223> OTHER INFORMATION: oligonucleotide

<400> SEQUENCE: 47
aaccgatttc ag                                                           12

<210> SEQ ID NO 48
<211> LENGTH: 9
<212> TYPE: DNA
<213> ORGANISM: Artificial
<220> FEATURE:
<223> OTHER INFORMATION: oligonucleotide

<400> SEQUENCE: 48 atggtgcta                                                                9

<210> SEQ ID NO 49
<211> LENGTH: 21
<212> TYPE: RNA
<213> ORGANISM: Homo sapiens
```

<400> SEQUENCE: 49
uagcagcaca gaaauauugg c    21

<210> SEQ ID NO 50
<211> LENGTH: 12
<212> TYPE: DNA
<213> ORGANISM: Artificial
<220> FEATURE:
<223> OTHER INFORMATION: oligonucleotide

<400> SEQUENCE: 50
gccaatattt ct    12

<210> SEQ ID NO 51
<211> LENGTH: 9
<212> TYPE: DNA
<213> ORGANISM: Artificial
<220> FEATURE:
<223> OTHER INFORMATION: oligonucleotide

<400> SEQUENCE: 51 gtgctgcta    9

<210> SEQ ID NO 52
<211> LENGTH: 22
<212> TYPE: RNA
<213> ORGANISM: Homo sapiens

<400> SEQUENCE: 52
uucaaguaau ccaggauagg cu    22

<210> SEQ ID NO 53
<211> LENGTH: 12
<212> TYPE: DNA
<213> ORGANISM: Artificial
<220> FEATURE:
<223> OTHER INFORMATION: oligonucleotide

<400> SEQUENCE: 53
agcctatcct gg    12

<210> SEQ ID NO 54
<211> LENGTH: 10
<212> TYPE: DNA
<213> ORGANISM: Artificial
<220> FEATURE:
<223> OTHER INFORMATION: oligonucleotide

<400> SEQUENCE: 54
attacttgaa    10

<210> SEQ ID NO 55
<211> LENGTH: 23
<212> TYPE: RNA
<213> ORGANISM: Homo sapiens

<400> SEQUENCE: 55
uaaagugcuu auagugcagg uag    23

<210> SEQ ID NO 56
<211> LENGTH: 12
<212> TYPE: DNA
<213> ORGANISM: Artificial
<220> FEATURE:
<223> OTHER INFORMATION: oligonucleotide -continued

```
<400> SEQUENCE: 56
ctacctgcac ta                                                         12

<210> SEQ ID NO 57
<211> LENGTH: 11
<212> TYPE: DNA
<213> ORGANISM: Artificial
<220> FEATURE:
<223> OTHER INFORMATION: oligonucleotide

<400> SEQUENCE: 57
taagcacttt a                                                          11

<210> SEQ ID NO 58
<211> LENGTH: 22
<212> TYPE: RNA
<213> ORGANISM: Homo sapiens

<400> SEQUENCE: 58
ucacagugaa ccggucucuu uc                                              22

<210> SEQ ID NO 59
<211> LENGTH: 12
<212> TYPE: DNA
<213> ORGANISM: Artificial
<220> FEATURE:
<223> OTHER INFORMATION: oligonucleotide

<400> SEQUENCE: 59
gaaagagacc gg                                                         12

<210> SEQ ID NO 60
<211> LENGTH: 10
<212> TYPE: DNA
<213> ORGANISM: Artificial
<220> FEATURE:
<223> OTHER INFORMATION: oligonucleotide

<400> SEQUENCE: 60
ttcactgtga                                                            10

<210> SEQ ID NO 61
<211> LENGTH: 24
<212> TYPE: RNA
<213> ORGANISM: Homo sapiens

<400> SEQUENCE: 61
uacugcauca ggaacugacu ggau                                            24

<210> SEQ ID NO 62
<211> LENGTH: 13
<212> TYPE: DNA
<213> ORGANISM: Artificial
<220> FEATURE:
<223> OTHER INFORMATION: oligonucleotide

<400> SEQUENCE: 62
atccagtcag ttc                                                        13

<210> SEQ ID NO 63
<211> LENGTH: 11
<212> TYPE: DNA
<213> ORGANISM: Artificial
<220> FEATURE:
<223> OTHER INFORMATION: oligonucleotide
```

```
<400> SEQUENCE: 63
ctgatgcagt a                                                            11

<210> SEQ ID NO 64
<211> LENGTH: 21
<212> TYPE: RNA
<213> ORGANISM: Homo sapiens

<400> SEQUENCE: 64
ugauugucca aacgcaauuc u                                                 21

<210> SEQ ID NO 65
<211> LENGTH: 12
<212> TYPE: DNA
<213> ORGANISM: Artificial
<220> FEATURE:
<223> OTHER INFORMATION: oligonucleotide

<400> SEQUENCE: 65
agaattgcgt tt                                                           12

<210> SEQ ID NO 66
<211> LENGTH: 9
<212> TYPE: DNA
<213> ORGANISM: Artificial
<220> FEATURE:
<223> OTHER INFORMATION: oligonucleotide

<400> SEQUENCE: 66 ggacaatca                                                                9

<210> SEQ ID NO 67
<211> LENGTH: 21
<212> TYPE: RNA
<213> ORGANISM: Homo sapiens

<400> SEQUENCE: 67
acagcaggca cagacaggca g                                                 21

<210> SEQ ID NO 68
<211> LENGTH: 11
<212> TYPE: DNA
<213> ORGANISM: Artificial
<220> FEATURE:
<223> OTHER INFORMATION: oligonucleotide

<400> SEQUENCE: 68
ctgcctgtct g                                                            11

<210> SEQ ID NO 69
<211> LENGTH: 10
<212> TYPE: DNA
<213> ORGANISM: Artificial
<220> FEATURE:
<223> OTHER INFORMATION: oligonucleotide

<400> SEQUENCE: 69
tgcctgctgt                                                              10

<210> SEQ ID NO 70
<211> LENGTH: 23
<212> TYPE: RNA
<213> ORGANISM: Homo sapiens
```

```
<400> SEQUENCE: 70
aucacauugc cagggauuac cac                                                23

<210> SEQ ID NO 71
<211> LENGTH: 12
<212> TYPE: DNA
<213> ORGANISM: Artificial
<220> FEATURE:
<223> OTHER INFORMATION: oligonucleotide

<400> SEQUENCE: 71
gtggtaatcc ct                                                            12

<210> SEQ ID NO 72
<211> LENGTH: 11
<212> TYPE: DNA
<213> ORGANISM: Artificial
<220> FEATURE:
<223> OTHER INFORMATION: oligonucleotide

<400> SEQUENCE: 72
ggcaatgtga t                                                             11

<210> SEQ ID NO 73
<211> LENGTH: 22
<212> TYPE: RNA
<213> ORGANISM: Homo sapiens

<400> SEQUENCE: 73
agugccgcag aguuuguagu gu                                                 22

<210> SEQ ID NO 74
<211> LENGTH: 12
<212> TYPE: DNA
<213> ORGANISM: Artificial
<220> FEATURE:
<223> OTHER INFORMATION: oligonucleotide

<400> SEQUENCE: 74
acactacaaa ct                                                            12

<210> SEQ ID NO 75
<211> LENGTH: 10
<212> TYPE: DNA
<213> ORGANISM: Artificial
<220> FEATURE:
<223> OTHER INFORMATION: oligonucleotide

<400> SEQUENCE: 75
ctgcggcact                                                               10

<210> SEQ ID NO 76
<211> LENGTH: 20
<212> TYPE: RNA
<213> ORGANISM: Homo sapiens

<400> SEQUENCE: 76
acugcaguga gggcacuugu                                                    20

<210> SEQ ID NO 77
<211> LENGTH: 11
<212> TYPE: DNA
<213> ORGANISM: Artificial
<220> FEATURE:
<223> OTHER INFORMATION: oligonucleotide
```

```
<400> SEQUENCE: 77
acaagtgccc t                                                          11

<210> SEQ ID NO 78
<211> LENGTH: 9
<212> TYPE: DNA
<213> ORGANISM: Artificial
<220> FEATURE:
<223> OTHER INFORMATION: oligonucleotide

<400> SEQUENCE: 78 cactgcagt                                                              9

<210> SEQ ID NO 79
<211> LENGTH: 23
<212> TYPE: RNA
<213> ORGANISM: Homo sapiens

<400> SEQUENCE: 79
aaaagcuggg uugagagggc gaa                                             23

<210> SEQ ID NO 80
<211> LENGTH: 12
<212> TYPE: DNA
<213> ORGANISM: Artificial
<220> FEATURE:
<223> OTHER INFORMATION: oligonucleotide

<400> SEQUENCE: 80
ttcgccctct ca                                                         12

<210> SEQ ID NO 81
<211> LENGTH: 11
<212> TYPE: DNA
<213> ORGANISM: Artificial
<220> FEATURE:
<223> OTHER INFORMATION: oligonucleotide

<400> SEQUENCE: 81
acccagcttt t                                                          11

<210> SEQ ID NO 82
<211> LENGTH: 22
<212> TYPE: RNA
<213> ORGANISM: Homo sapiens

<400> SEQUENCE: 82
ugagguagua gguuguauag uu                                              22

<210> SEQ ID NO 83
<211> LENGTH: 12
<212> TYPE: DNA
<213> ORGANISM: Artificial
<220> FEATURE:
<223> OTHER INFORMATION: oligonucleotide

<400> SEQUENCE: 83
aactatacaa cc                                                         12

<210> SEQ ID NO 84
<211> LENGTH: 10
<212> TYPE: DNA
<213> ORGANISM: Artificial
<220> FEATURE:
<223> OTHER INFORMATION: oligonucleotide
```

```
<400> SEQUENCE: 84
tactacctca                                                          10

<210> SEQ ID NO 85
<211> LENGTH: 22
<212> TYPE: RNA
<213> ORGANISM: Homo sapiens

<400> SEQUENCE: 85
ugagguagua gguugugugg uu                                            22

<210> SEQ ID NO 86
<211> LENGTH: 12
<212> TYPE: DNA
<213> ORGANISM: Artificial
<220> FEATURE:
<223> OTHER INFORMATION: oligonucleotide

<400> SEQUENCE: 86
aaccacacaa cc                                                       12

<210> SEQ ID NO 87
<211> LENGTH: 10
<212> TYPE: DNA
<213> ORGANISM: Artificial
<220> FEATURE:
<223> OTHER INFORMATION: oligonucleotide

<400> SEQUENCE: 87
tactacctca                                                          10

<210> SEQ ID NO 88
<211> LENGTH: 22
<212> TYPE: RNA
<213> ORGANISM: Homo sapiens

<400> SEQUENCE: 88
ugagguagua gguuguaugg uu                                            22

<210> SEQ ID NO 89
<211> LENGTH: 12
<212> TYPE: DNA
<213> ORGANISM: Artificial
<220> FEATURE:
<223> OTHER INFORMATION: oligonucleotide

<400> SEQUENCE: 89
aaccatacaa cc                                                       12

<210> SEQ ID NO 90
<211> LENGTH: 10
<212> TYPE: DNA
<213> ORGANISM: Artificial
<220> FEATURE:
<223> OTHER INFORMATION: oligonucleotide

<400> SEQUENCE: 90
tactacctca                                                          10

<210> SEQ ID NO 91
<211> LENGTH: 22
<212> TYPE: RNA
<213> ORGANISM: Homo sapiens
```

<400> SEQUENCE: 91
ugagguagua guuuguacag ua    22

<210> SEQ ID NO 92
<211> LENGTH: 12
<212> TYPE: DNA
<213> ORGANISM: Artificial
<220> FEATURE:
<223> OTHER INFORMATION: oligonucleotide

<400> SEQUENCE: 92
tactgtacaa ac    12

<210> SEQ ID NO 93
<211> LENGTH: 10
<212> TYPE: DNA
<213> ORGANISM: Artificial
<220> FEATURE:
<223> OTHER INFORMATION: oligonucleotide

<400> SEQUENCE: 93
tactacctca    10

<210> SEQ ID NO 94
<211> LENGTH: 10
<212> TYPE: DNA
<213> ORGANISM: Artificial
<220> FEATURE:
<223> OTHER INFORMATION: oligonucleotide

<400> SEQUENCE: 94
tacgcgtata    10

<210> SEQ ID NO 95
<211> LENGTH: 10
<212> TYPE: DNA
<213> ORGANISM: Artificial
<220> FEATURE:
<223> OTHER INFORMATION: oligonucleotide

<400> SEQUENCE: 95
aacgcgtata    10

<210> SEQ ID NO 96
<211> LENGTH: 24
<212> TYPE: RNA
<213> ORGANISM: Homo sapiens

<400> SEQUENCE: 96
gggaauaccg ggugcuguag gcuu    24

<210> SEQ ID NO 97
<211> LENGTH: 13
<212> TYPE: DNA
<213> ORGANISM: Artificial
<220> FEATURE:
<223> OTHER INFORMATION: oligonucleotide

<400> SEQUENCE: 97
aagcctacag cac    13

<210> SEQ ID NO 98
<211> LENGTH: 11
<212> TYPE: DNA
<213> ORGANISM: Artificial

-continued

```
<220> FEATURE:
<223> OTHER INFORMATION: oligonucleotide

<400> SEQUENCE: 98
ccggtattcc c                                                              11
```